(12) United States Patent
Fallon

(10) Patent No.: US 9,624,525 B2
(45) Date of Patent: *Apr. 18, 2017

(54) METHOD FOR TREATING PERVASIVE DEVELOPMENT DISORDERS

(75) Inventor: Joan M. Fallon, Bronxville, NY (US)

(73) Assignee: Curemark, LLC, Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/313,629

(22) Filed: Dec. 7, 2011

(65) Prior Publication Data

US 2012/0114562 A1    May 10, 2012

Related U.S. Application Data

(60) Division of application No. 12/283,090, filed on Sep. 8, 2008, now Pat. No. 8,105,584, which is a continuation of application No. 10/681,018, filed on Oct. 8, 2003, now Pat. No. 8,163,278, which is a continuation of application No. 09/707,395, filed on Nov. 7, 2000, now Pat. No. 6,632,429, which is a continuation-in-part of application No. 09/466,559, filed on Dec. 17, 1999, now Pat. No. 6,534,063.

(51) Int. Cl.

| | | |
|---|---|---|
| *A61K 38/54* | (2006.01) | |
| *A61K 35/39* | (2015.01) | |
| *A61K 35/37* | (2015.01) | |
| *C12Q 1/37* | (2006.01) | |
| *G01N 30/00* | (2006.01) | |
| *A61K 38/22* | (2006.01) | |

(52) U.S. Cl.
CPC ............ *C12Q 1/37* (2013.01); *A61K 38/2235* (2013.01); *G01N 2333/976* (2013.01); *Y10S 435/803* (2013.01); *Y10T 436/24* (2015.01)

(58) Field of Classification Search
CPC ....... A61B 5/168; A61B 5/165; A61B 5/4076; A61B 5/4833; A61K 38/54
See application file for complete search history.

(56) References Cited

U.S. PATENT DOCUMENTS

| | | |
|---|---|---|
| 3,002,883 A | 10/1961 | Butt et al. |
| 3,223,594 A | 12/1965 | Serge |
| 3,322,626 A | 5/1967 | D'Argento |
| 3,357,894 A | 12/1967 | Jose et al. |
| 3,515,642 A | 6/1970 | Mima et al. |
| 3,574,819 A | 4/1971 | Gross et al. |
| 3,860,708 A | 1/1975 | Prout |
| 3,940,478 A | 2/1976 | Kurtz |
| 4,079,125 A | 3/1978 | Sipos |
| 4,145,410 A | 3/1979 | Sears |
| 4,241,046 A | 12/1980 | Papahadjopoulos et al. |
| 4,280,971 A | 7/1981 | Wischniewski et al. |
| 4,447,412 A | 5/1984 | Bilton |
| 4,456,544 A | 6/1984 | Lupova et al. |
| 4,623,624 A | 11/1986 | Schultze |
| 4,826,679 A | 5/1989 | Roy |
| 5,190,775 A | 3/1993 | Klose |
| 5,227,166 A | 7/1993 | Ueda et al. |
| 5,250,418 A | 10/1993 | Moller et al. |
| 5,324,514 A | 6/1994 | Sipos |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,607,863 A | 3/1997 | Chandler |
| 5,648,335 A | 7/1997 | Lewis et al. |
| 5,674,532 A | 10/1997 | Atzl et al. |
| 5,686,311 A | 11/1997 | Shaw |

(Continued)

FOREIGN PATENT DOCUMENTS

| | | |
|---|---|---|
| CA | 2198317 A1 | 2/1997 |
| CA | 2263703 A1 | 8/1999 |

(Continued)

OTHER PUBLICATIONS

Eaves RC et al. (1993) The criterion-related validity of the Childhood Autism Rating Scale and the Autism Behavior Checklist. J. Abnorm. Child Psychol. 21(5):481-491; abstract only.*
Childhood Autism Rating Scale (CARS), Wikipedia, downloaded May 5, 2014.*
U.S. Appl. No. 13/002,136, filed Dec. 30, 2010, Fallon.
U.S. Appl. No. 13/144,286, filed Jul. 12, 2011, Fallon et al.
U.S. Appl. No. 13/144,290, filed Jul. 12, 2011, Fallon et al.
U.S. Appl. No. 13/204,881, filed Aug. 8, 2011, Fallon et al.
U.S. Appl. No. 13/208,963, filed Aug. 12, 2011, Fallon.
U.S. Appl. No. 13/271,783, filed Oct. 12, 2011, Fallon.
U.S. Appl. No. 13/313,708, filed Dec. 7, 2011, Fallon.
Adams. "Summary of Defeat Autism Now! (DNN!) Oct. 2001 Conference," retrieved from the internet Dec. 18, 2008. http://puterakembara.org/rm/DAN2001.htm.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.

(Continued)

*Primary Examiner* — Kimberly A. Ballard
(74) *Attorney, Agent, or Firm* — Wilson Sonsini Goodrich & Rosati

(57) ABSTRACT

A method of utilizing the chymotrypsin level of an individual as a measure of the success of neuropeptides, and peptides or digestive enzyme administration to such individuals, and in particular, as a prognosticative of potential neuropeptides, peptides, and digestive enzyme administration for persons having ADD, ADHD, Autism and other PDD related disorders. A method for determining the efficacy of neuropeptides, peptides, or digestive enzymes for the treatment of an individual diagnosed with a pervasive developmental disorder (PDD) comprises obtaining a sample of feces from an individual, determining a quantitative level of chymotrypsin present in the sample, and correlating the quantitative level of chymotrypsin determined to be present in the sample with the PDD to determine the efficacy of treating the individual with neuropeptides, peptides, or digestive enzyme administration.

28 Claims, 17 Drawing Sheets

(56) References Cited

U.S. PATENT DOCUMENTS

| | | |
|---|---|---|
| 5,750,104 A | 5/1998 | Sipos |
| 5,753,223 A | 5/1998 | Shibahara et al. |
| 5,776,917 A | 7/1998 | Blank et al. |
| 5,858,758 A | 1/1999 | Hillman et al. |
| 5,952,178 A | 9/1999 | Lapidus et al. |
| 5,958,875 A | 9/1999 | Longo et al. |
| 5,977,175 A | 11/1999 | Lin |
| 5,985,891 A | 11/1999 | Rowe |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |
| 6,096,338 A | 8/2000 | Lacy et al. |
| 6,100,080 A | 8/2000 | Johansen |
| 6,149,585 A | 11/2000 | Gray |
| 6,153,236 A | 11/2000 | Wu et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,238,727 B1 | 5/2001 | Takemoto et al. |
| 6,251,478 B1 | 6/2001 | Pacifico et al. |
| 6,261,602 B1 | 7/2001 | Calanchi et al. |
| 6,261,613 B1 | 7/2001 | Narayanaswamy et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,632,429 B1 | 10/2003 | Fallon |
| 6,660,831 B2 | 12/2003 | Fallon |
| 6,699,885 B2 | 3/2004 | Phillips |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander et al. |
| 7,129,053 B1 | 10/2006 | Reiter et al. |
| 7,138,123 B2 | 11/2006 | Fallon |
| 7,244,412 B2 | 7/2007 | Lin |
| 7,285,633 B2 | 10/2007 | Wu et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,211,661 B2 | 7/2012 | Fallon |
| 8,221,747 B2 | 7/2012 | Ortenzi et al. |
| 8,437,689 B2 | 5/2013 | Mazar |
| 8,486,390 B2 | 7/2013 | Fallon |
| 8,613,918 B2 | 12/2013 | Fallon |
| 8,921,054 B2 | 12/2014 | Fallon |
| 8,980,252 B2 | 3/2015 | Fallon |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 9,084,784 B2 | 7/2015 | Fallon et al. |
| 9,107,419 B2 | 8/2015 | Fallon et al. |
| 9,233,146 B2 | 1/2016 | Fallon et al. |
| 9,320,780 B2 | 4/2016 | Fallon |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0259995 A1 | 11/2006 | Cayouette et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0187525 A1 | 8/2008 | Porubcan |
| 2008/0199448 A1 | 8/2008 | Ross et al. |
| 2008/0248558 A1 | 10/2008 | Deinhammer et al. |
| 2008/0254009 A1 | 10/2008 | Finegold |
| 2008/0274174 A1 | 11/2008 | Ortenzi et al. |

(56) References Cited

U.S. PATENT DOCUMENTS

| | | |
|---|---|---|
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0110674 A1 | 4/2009 | Loizou |
| 2009/0117180 A1 | 5/2009 | Ortenzi et al. |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon |
| 2012/0027848 A1 | 2/2012 | Fallon |
| 2012/0070504 A1 | 3/2012 | Fallon |
| 2012/0128764 A1 | 5/2012 | Venkatesh et al. |
| 2012/0201875 A1 | 8/2012 | Ortenzi et al. |
| 2012/0258149 A1 | 10/2012 | Fallon et al. |
| 2014/0348881 A1 | 11/2014 | Fallon |
| 2015/0023944 A1 | 1/2015 | Fallon |
| 2015/0140550 A1 | 5/2015 | Fallon |
| 2015/0147308 A1 | 5/2015 | Fallon et al. |
| 2015/0150955 A1 | 6/2015 | Fallon et al. |
| 2015/0174219 A1 | 6/2015 | Fallon |
| 2015/0174220 A1 | 6/2015 | Fallon |
| 2015/0246104 A1 | 9/2015 | Fallon et al. |
| 2015/0246105 A1 | 9/2015 | Fallon et al. |
| 2015/0273030 A1 | 10/2015 | Fallon |
| 2015/0335589 A1 | 11/2015 | Fallon et al. |
| 2016/0045576 A1 | 2/2016 | Fallon et al. |
| 2016/0206708 A1 | 7/2016 | Fallon |
| 2016/0213697 A1 | 7/2016 | Fallon |
| 2016/0266113 A1 | 9/2016 | Fallon |

FOREIGN PATENT DOCUMENTS

| | | | |
|---|---|---|---|
| CN | 1031562 A | | 3/1989 |
| CN | 1329923 A | | 1/2002 |
| DE | 3738599 A1 | | 5/1989 |
| DE | 4332985 | | 3/1995 |
| DE | 202010004926 U1 | | 7/2010 |
| EP | 0425214 A2 | | 5/1991 |
| EP | 0436110 A1 | | 7/1991 |
| EP | 0451484 A1 | | 10/1991 |
| EP | 0564739 A2 | | 10/1993 |
| EP | 0564739 A3 | | 4/1995 |
| EP | 1162995 B1 | | 6/2003 |
| EP | 1413202 A1 | | 4/2004 |
| EP | 1335706 B1 | | 4/2005 |
| EP | 1019072 B1 | * | 5/2005 |
| EP | 1604677 A1 | | 12/2005 |
| EP | 1931317 B1 | | 6/2008 |
| EP | 2258837 A1 | | 12/2010 |
| GB | 669782 A | | 4/1952 |
| GB | 2347742 A | | 9/2000 |
| JP | 62230714 A | | 10/1987 |
| JP | H 04-364119 A | | 12/1992 |
| JP | 2003517831 A | | 6/2003 |
| JP | 2005515223 A | | 5/2005 |
| JP | 2006512091 A | | 4/2006 |
| JP | 2007523664 A | | 8/2007 |
| JP | 2008-283895 A | | 11/2008 |
| KR | 20050084485 A | | 8/2005 |
| RU | 2356244 C1 | | 5/2009 |
| TW | 310277 B | | 7/1997 |
| WO | WO 84/02846 A1 | | 8/1984 |
| WO | WO 90/02562 A1 | | 3/1990 |
| WO | WO 94/19005 A1 | | 9/1994 |
| WO | WO 95/22344 A1 | | 8/1995 |
| WO | WO 97/32480 A1 | | 9/1997 |
| WO | WO 98/22499 A2 | | 5/1998 |
| WO | WO-9826807 A1 | | 6/1998 |
| WO | WO 98/22499 A3 | | 7/1998 |
| WO | WO-9832336 A2 | | 7/1998 |
| WO | WO 98/52593 A1 | | 11/1998 |
| WO | WO 99/64059 A2 | | 12/1999 |
| WO | WO 00/09142 A1 | | 2/2000 |
| WO | WO 99/64059 A3 | | 3/2000 |
| WO | WO 00/21504 A1 | | 4/2000 |
| WO | WO 01/27612 A2 | | 4/2001 |
| WO | WO 01/43764 A2 | | 6/2001 |
| WO | WO 01/45835 A1 | | 6/2001 |
| WO | WO 01/27612 A3 | | 10/2001 |
| WO | WO 01/43764 A3 | | 11/2001 |
| WO | WO 02/14537 A2 | | 2/2002 |
| WO | WO-0219828 A1 | | 3/2002 |
| WO | WO 02/14537 A3 | | 5/2002 |
| WO | WO 02/051352 A2 | | 7/2002 |
| WO | WO 02/051436 A2 | | 7/2002 |
| WO | WO 03/051345 A2 | | 6/2003 |
| WO | WO 03/059088 A1 | | 7/2003 |
| WO | WO 2004/060074 A1 | | 7/2004 |
| WO | WO-2004093883 A2 | | 11/2004 |
| WO | WO 2005/115445 A1 | | 12/2005 |
| WO | WO 2006/031554 A2 | | 3/2006 |
| WO | WO 2006/044529 A1 | | 4/2006 |
| WO | WO 2006/031554 A3 | | 9/2006 |
| WO | WO 2007/002572 A2 | | 1/2007 |
| WO | WO 2007/074454 A2 | | 7/2007 |
| WO | WO 2007/147714 A1 | | 12/2007 |
| WO | WO 2008/021987 A2 | | 2/2008 |
| WO | WO 2008/102264 A2 | | 8/2008 |
| WO | WO 2009/114757 A2 | | 9/2009 |
| WO | WO 2009/155689 A1 | | 12/2009 |
| WO | WO 2010/002972 A1 | | 1/2010 |
| WO | WO 2010/025126 A1 | | 3/2010 |
| WO | WO 2010/080830 A1 | | 7/2010 |
| WO | WO 2010/080835 A1 | | 7/2010 |
| WO | WO 2010/120781 A1 | | 10/2010 |
| WO | WO 2011/000924 A1 | | 1/2011 |
| WO | WO 2011/114225 A1 | | 9/2011 |

OTHER PUBLICATIONS

Amendment dated Nov. 17, 2007 in Reply to Restriction Requirement dated Oct. 17, 2007 for U.S. Appl. No. 11/555,697.

Amendment dated Dec. 12, 2007 in Reply to Office Action dated Aug. 8, 2007 for U.S. Appl. No. 11/213,382.

Amendment dated Dec. 7, 2007 in Reply to Office Action dated Aug. 7, 2007 for U.S. Appl. No. 10/681,018.

Amendment dated Feb. 2, 2004 in Reply to Office Action dated Jul. 29, 2003 for U.S. Appl. No. 09/990,909.

Amendment dated Feb. 29, 2008 in Reply to Notice of Non-Responsive Amendment dated Feb. 11, 2008 for U.S. Appl. No. 11/555,697.

Amendment dated Feb. 7, 2003 in Reply to Office Action dated Jul. 30, 2002 for U.S. Appl. No. 09/990,909.

Amendment dated Feb. 2, 2009 in Reply to Office Action dated Aug. 18, 2008 for U.S. Appl. No. 10/681,018.

Amendment dated Mar. 1, 2004 in Reply to Office Action dated Aug. 26, 2003 for U.S. Appl. No. 10/041,073.

Amendment dated Mar. 24, 2010 in Reply to Final Office Action dated Sep. 24, 2009 for U.S. Appl. No. 12/046,252.

(56) References Cited

OTHER PUBLICATIONS

Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Ang, et al. Biological role and regulation of the universally conserved heat shock proteins. J Biol Chem. Dec. 25, 1991;266(36):24233-6.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
Austic. Development and adaptation of protein digestion. J Nutr. May 1985;115(5):686-97.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod. Secretin Treatment for Gastrointestinal Dysmobility in Patients with Familial Dysautonomia. New York University School of Medicine, Grant Recipient awards, Mar-May 2000. www.med.nyu.edu/ogars/awards/awards2000/page2.html.
Azilect et al. "Correlation between protein intake and daily levodopa dosage," Obtained from the internet May 2, 2007, www.azilect.eu/media/cnsnews/showitem.aspx?i=d1c603e4-3c61-4aal-a376-6e519a5a0f80.
Barlow. A comparison of the blood pressure, kidney volume and the pancreatic secretory response following the vein administration of various secretin preparations. Am J Phys. 1927;81:182-188.
Beilmann, et al. Neoexpression of the c-met/hepatocyte growth factor-scatter factor receptor gene in activated monocytes. Blood. Dec. 1, 1997;90(11):4450-8.
Belmonte et al. Fragile X syndrome and autism at the intersection of genetic and neural networks. Nat Neurosci. Oct 2006; 9(10):1221-5 (abstract only).
Blackmer. Parkinson disease: treatment and medication. Mar. 10, 2009., retrieved from the internet on Sep. 15, 2009, emedicine.medscape.com/article/312519-treatment.
Bode et al. Usefulness of a simple photometric determination of chymotrypsin activity in stools—results of a multicentre study. Clin Biochem. 1986; 19:333-37.

Borowitz, et al. Use of pancreatic enzyme supplements for patients with cystic fibrosis in the context of fibrosing colonopathy. Consensus Committee. J Pediatr. Nov. 1995;127(5):681-4.
Boyd, et al. Positively charged amino acid residues can act as topogenic determinants in membrane proteins. Proc Natl Acad Sci U S A. Dec. 1989;86(23):9446-50.
Brudnak et al. Enzyme-based therapy for autism spectrum disorders—is it worth another look? Med Hypoth. 2002; 58:422-428.
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Campbell et al. A genetic variant that disrupts MET transcription is associated with autism. Proc Natl Acad Sci USA. 2006; 103(45):16834-16839.
Carlton. Autism and malnutrition: the milk connection. Retrieved from the internet on Feb. 18, 2008, www.mercola.com/2004/autism_malnutrition.htm.
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
Chen, et al. Identification of two lysosomal membrane glycoproteins. J Cell Biol. Jul. 1985;101(1):85-95.
Cichoke, et al. The complete book of enzyme therapy. Penguin. 1998: 39, 42, 47, 50, and 53.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Craig, et al. Heat shock proteins: molecular chaperones of protein biogenesis. Microbiol Rev. Jun. 1993;57(2):402-14.
Croonenberghs, et al. Peripheral markers of serotonergic and noradrenergic function in post-pubertal, caucasian males with autistic disorder. Neuropsychopharmacology. Mar. 2000;22(3):275-83.
Cruse et al. Illustrated dictionary of immunology. CRC Press, New York. 1995.
Darman. An introduction to alternative medicine for psychiatric conditions. Oct. 22, 2007, retrieved on Sep. 18, 2009, web.archive.org/web/20071022104238/http://altp[therapies4bipolar.info/ortho/html.
Derwent. English abstract for RU 2286785 Nov. 10, 2006. Downloaded from the Derwent file Jul. 13, 2011.
Digestive Enzyme Wikipedia. Retrieved from the Internet Sep. 10, 2009, en.wikipedia.org/wiki/Digestive_enzyme.
Dobbs et al. Link between helicobacter pylori infection and idiopathic parkinsonism. Medical Hypothsis. 2000; 55(2):93-98.
Dockter et al. Determination of chymotrypsin in the feces by a new photometric method. Padiatr Padol. 1985; 20(3):257-265.
Edelson, et al. 3-Cyclohexene-1-glycine, an Isoleucine Antagonist. J. Am. Chem. Soc. 1958; 80(11):2698-2700.
Ethridge, et al. Acute pancreatitis results in induction of heat shock proteins 70 and 27 and heat shock factor-1. Pancreas. Oct. 2000;21(3):248-56.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.

(56) References Cited

OTHER PUBLICATIONS

Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):56-515.
Fitzsimmons, et al. High-dose pancreatic-enzyme supplements and fibrosing colonopathy in children with cystic fibrosis. N Engl J Med. May 1, 1997;336(18):1283-9.
Garcia et al. Detection of giardia lamblia, entamoeba histolytica/entamoeba dispar, and cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Giglio, et al. Failure to thrive: the earliest feature of cystic fibrosis in infants diagnosed by neonatal screening. Acta Paediatr. Nov. 1997;86(11):1162-5.
Goff, et al. Production of abnormal proteins in E. coli stimulates transcription of Ion and other heat shock genes. Cell. Jun. 1985;41(2):587-95.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
Heijerman, et al. Omeprazole enhances the efficacy of pancreatin (pancrease) in cystic fibrosis. Ann Intern Med. Feb. 1, 1991;114(3):200-1.
Hendren et al. Mechanistic biomarkers for autism treatment. Medical Hypotheses. 2009; 73:950-954.
Horvath et al. Improved social and language skills after secretin administration in patients with autistic spectrum disorders. Journal of the Association for Academic Minority Physicians. Jan. 1998; 9(1):9-15.
Horvath, et al. Gastrointestinal abnormalities in children with autistic disorder. J Pediatr. Nov. 1999;135(5):559-63.
Hoshiko et al. The effect of the gastrointestinal hormones on colonic muscosal blood flow. Acta Medica Nagasakiensia. 1994; 39(4):125-130.
Huang, et al. Apoptotic cell death in mouse models of GM2 gangliosidosis and observations on human Tay-Sachs and Sandhoff diseases. Hum Mol Genet. Oct. 1997;6(11): 1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
Juhl. Fibromyalgia and the serotonin pathway. Altern Med Rev. 1998; 3(5):367-375.
Kachrimanis, et al. Tensile strength and disintegration of tableted silicified microcrystalline cellulose: influences of interparticle bonding. J Pharm Sci. Jul. 2003:92(7): 1489-501.
Kaspar et al. New photometric assay for chymotrypsin in stool. Clinical Chemistry. 1984; 30(11):1753-1757.
Koller, et al. Falls and Parkinson's Disease (Abstract). Clin Neuropharmacol. 1989; 12(2):98-105.
Koster et al. Evidence based medicine and extradigestive manifestations of helocobacter pylori. Acta Gastro-Enterologica Belgica. 2000; 63(4):388-392.
Lashkari, et al. Williams-Beuren syndrome: An update and review for the primary physician. Clinical Pediatrics. 1999; 38(4):189-208.
Layer et al. Pancreatin enzyme replacement therapy. Current Gastroenterology Reports. 2001; 3:101-108.
Levy, et al. Relationship of dietary intake to gastrointestinal symptoms in children with autistic spectrum disorders. Biol Psychiatry. Feb. 15, 2007;61(4):492-7.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacReady. Parkinson's Diseasne Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.
Marczewska et al. Protein intake in parkinsonian using the EPIC food frequency questionnaire. Mov Diord. Aug. 2006; 21(8):1229-1231.
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of parkinson's disease. Psychosomatics. 2000; 41(1):15-23.
Mayo Clinic Staff. Autism. Retrieved from internet Mar. 10, 2008, www.mayoclinic.com/health/autism/DS00348DSECTION=2.

(56) References Cited

OTHER PUBLICATIONS

Mayo Clinic Staff. Bipolar disorder. Jan. 4, 2008, www.mayoclinic.com/health/bipolardisorder/DS00356/DSECTION=symptoms.
Mayo Clinic Staff. Obsessive-compulsive disorder. Dec. 21, 2006. www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, www.mayoclinic.com/health/oppositional-defiant-disorder/DS00630/DSECTION=symptoms.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
Medsafe. Data sheet for alpha-lactose, Jul. 21, 1999, www.medsafe.govt.nz/Profs/Datasheet/a/Alphalactulosesyrup.htm.
Melmed, et al. Metabolic markers and gastrointestinal symptoms in children with autism and related disorders. J Pediatr Gast Nutr. 2000; 31:S31-S32.
Merck. Autism, Merck manual online medical library home addition, retrieved from the internet Mar. 10, 2008, www.mercl.com/mmhge/sec23/ch286/ch286b.html.
MeSH browser. "Child Development Disorders, Pervasive," and "Attention Deficit and Disruptive Behavior Disorders," National Library of medicine. 2001, www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michell et al. Biomarkers and parkinson's disease. Brain. 2004; 127(8):1693-1705.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Munasinghe et al. Digestive enzyme supplementation for autism spectrum disorders: a double-blind randomized controlled trial. J Autism Dev Disord. Sep. 2010;40(9):1131-8. Abstract only.
Nachaegari et al. Coprocessed excipients for solid dosage forms. Pharmaceutical Technology. 2004; p. 52, 54, 56 ,58, 60, 64.
Neuer, et al. The role of heat shock proteins in reproduction. Hum Reprod Update. Mar.-Apr. 2000;6(2):149-59.
Nevo et al. Acute immune polyneuropathies: correlations of serum antibodies to campylobacter jejuni and helicobacter pylori with anti-gm antibodies and clinical patterns of disease. J of Inf diseases. 1997; 175(S2):S154-6.
Ninds Dysautonimia Information Page retrieved from the internet Sep. 10, 2009, www.ninds.nih.gov/disorders/dysautonomia/dysautonomia.htm.
Ninds Guillain-Barre Syndrome Information Page retrieved from the internet Sep. 15, 2009, www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of Allowance dated Feb. 17, 2012 for U.S. Appl. No. 10/681,018.
Notice of Allowance dated Apr. 15, 2011 for U.S. Appl. No. 12/487,868.
Notice of Allowance dated Apr. 29, 2011 for U.S. Appl. No. 12/046,402.
Notice of Allowance dated May 23, 2011 for U.S. Appl. No. 09/990,909.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of Allowance dated Jul. 8, 2011 for U.S. Appl. No. 12/046,402.
Notice of Allowance dated Aug. 8, 2011 for U.S. Appl. No. 12/426,794.
Notice of Allowance dated Sep. 20, 2011 for U.S. Appl. No. 12/283,090.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
Office action dated Jan. 12, 2012 for U.S. Appl. No. 12/047,818.
Office Action dated Feb. 1, 2012 for U.S. Appl. No. 12/493,122.
Office Action dated Mar. 29, 2011 for U.S. Appl. No. 12/054,343.
Office Action dated Mar. 30, 2011 for U.S. Appl. No. 12/786,739.
Office Action dated Apr. 27, 2011 for U.S. Appl. No. 10/681,018.
Office Action dated Apr. 28, 2011 for U.S. Appl. No. 12/283,090.
Office Action dated May 24, 2011 for U.S. Appl. No. 12/487,864.
Office action dated Jun. 29, 2011 for U.S. Appl. No. 11/555,697.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office Action dated Oct. 1, 2001 for U.S. Appl. No. 09/466,559.
Office action dated Oct. 19, 2011 for U.S. Appl. No. 12/386,051.
Office Action dated Oct. 5, 2010 for U.S. Appl. No. 12/046,402.
Office Action dated Nov. 14, 2007 for U.S. Appl. No. 11/213,255.
Office Action dated Nov. 15, 2010 for U.S. Appl. No. 12/238,415.
Office Action dated Nov. 25, 2009 for U.S. Appl. No. 11/232,180.
Office Action dated Nov. 26, 2001 for U.S. Appl. No. 09/466,559.
Office action dated Dec. 15, 2011 for U.S. Appl. No. 12/493,147.
Office Action dated Dec. 19, 2005 for U.S. Appl. No. 10/730,567.
Office Action dated Dec. 22, 2006 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of crytosporidium oocysts in untreated stool specimens. J Clin Microbiol. 1995; 33(7):1963-1965.

(56) References Cited

OTHER PUBLICATIONS

Perman et al. Role of ph in production of hydrogen from carbohydrates by colonic bacterial flora. J Clin Invest. 1981; 24(4):684-685.
Peters et al. Prevalence of enteric parasites in homosexual patients attending an outpatient clinic. J of Clin Micro. 1986; 24(4):684-685.
Preliminary Amendment dated May 18, 2009 for U.S. Appl. No. 12/046,252.
Puri, et al. Isolated segmental duodenal ganglionosis. Indian Journal of Radiology and Imaging. 2000; 153-154.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Remtulla et al. Stool chymotrypsin activity measured by a spectrophotometric procedure to identify pancreat disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Rider, et al. Perspective of biochemical research in the neuronal ceroid-lipofuscinosis. Am J Med Genet. Feb. 15, 1992;42(4):519-24.
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Sabra, et al. Linkage of ileal-lymphoid-nodular hyperplasia (ILNH), food allergy and CNS developmental: evidence for a non-IgE association. Ann Aller Asth Immunol. 1999; 82(1):81.
Sandler et al. Short term benefit from oral vancomycin treatment of regressive-onset autism. J of Child Neuro. 2000; 15(7):42-435.
Sandler, et al. Lack of benefit of a single dose of synthetic human secretin in the treatment of autism and pervasive developmental disorder. N Engl J Med. Dec. 9, 1999;341(24):1801-6.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.

Schreck et al. Food preferences and factors influecing food selectivity for children with autism spectrum disorders. Res Develop Disabil. 2006; 27:353-363.
Seneca et al. Enhancement of brain 1-dopa concetration with a-chymotrypsm. J American Geriatrics Society. 1973; 256-258.
Sherwood et al. A new class of high-functionality excipients: silicified microcrystalline cellulose. Pharm Tech. 1998; 22(10):78-88.
Singh, et al. Plasma increase of interleukin-12 and interferon-gamma. Pathological significance in autism. J Neuroimmunol. May 1996;66(1-2):143-5.
Skeels et al. Crytosporidium infection in Oregon public health clinic patients 1985-88: the value of statewide laboratory surveillance. AJPH. 1990; 80(3):305-308.
Smith, et al. Fecal chymotrypsin and trypsin determinations. Canadian Medical Association Journal. 1971; 104(8):691-4 and 697.
Stein, et a. Nitrogen Metabolism in normal and hyperkinetic boys. Am J Clin Nutr. 1984; 39:520-524.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Stoll, et al. Enteral nutrient intake level determines intestinal protein synthesis and accretion rates in neonatal pigs. Am J Physiol Gastrointest Liver Physiol. Aug. 2000;279(2):G288-94.
Strader, et al. Publication Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Supplemental Amendment and Response dated Jun. 8, 2010 to Restriction Requirement dated Oct. 7, 2009 for U.S. Appl. No. 12/283,090.
The Alzheimer's Association. Basics of Alzheimer's Disease. 2005, 32 pages. www.alz.org/national/documents/brochure_Basicsofalz_low/pdf.
THEFREEDICTIONARY. Term Sprinkles. Www.thefreedictionary.com. Accessed Nov. 2, 2011. 1 page.
Thomas, et al. Defective protein folding as a basis of human disease. Trends Biochem Sci. Nov. 1995;20(11):456-9.
Tran, et al. Treatment of complex regional pain syndrome: a review of the evidence. Can J Anaesth. Feb. 2010;57(2):149-66.
Tsang et al. Extragastroduodenal conditions associated with Heliobacter pylori infection. Hong Kong Medical Journal. 1999; 5(2):169-174.
USP (32)-NF(27) 2009, Pancreatin, V.3, pp. 3194-3195.
Vilanova, et al. Preparative isolation of the two forms of pig pancreatic pro-(carboxypeptidase A) and their monomeric carboxypeptidases A. Biochem J. Aug. 1, 1985;229(3):605-9.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Walsh, et al. Heat shock and the role of the HSPs during neural plate induction in early mammalian CNS and brain development. Cell Mol Life Sci. Feb. 1997;53(2):198-211.
Weintraub, et al. Morphometric studies of pancreatic acinar granule formation in NCTR-Balb/c mice. J Cell Sci. May 1992;102 ( Pt 1):141-7.

(56) References Cited

OTHER PUBLICATIONS

Wender et al. Prevalence of attention deficit disorder, residual type, and other psychiatric disorders in patients with irritable colon syndrome. Am J Psychiatry. 1983; 140(12):1579-82 Abstract only.
Williams, et al. Eating habits of children with autism. Pediatr Nurs. May-Jun. 2000;26(3):259-64.
Wohlman et al. Enhancement of drug activity by chymotrypsin, penicillin penetration into granulomatous sesions and inflammatory fluids. Cellular and Molecular Life Sciences. 1969; 25(9):953-954.
Woodward et al. Ischaemic enterocolitis complicating aidiopathic dysatuonomia. Gut. 1998; 43:285-287.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
Zhang et al. Lactulose-mannitol intestinal permeability test in children with diarrhea caused by rotavirus abd cryptosporidium. J of Pediatric Gastro & Nutrition. 2000; 31(1):16-21.
U.S. Appl. No. 13/757,412, filed Feb. 1, 2013, Fallon et al.
Mitsui, et al. Role of aminopepridases in the blood pressure regulation. Biological and Pharmaceutical Bulletin of Japan, Pharmaceutical Sociey of Japan. 2004; 27(6):768-771.
Office action dated Mar. 5, 2013 for U.S. Appl. No. 12/493,122.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. www.fda.gov/drugs/drugsafety/ucm290510.htm.
U.S. Appl. No. 13/448,061, filed Apr. 16, 2012, Fallon.
Elkashef, et al. Biological markers of cocaine addiction: implications for medications development. Addict Biol. Jun. 2003;8(2):123-39.
Fallon. Could one of the most widely prescribed antibiotics amoxicillin/clavulanate "augmentin" be a risk factor for autism? Med Hypotheses. 2005;64(2):312-5.
Horvath, et al. Autism and gastrointestinal symptoms. Curr Gastroenterol Rep. Jun. 2002;4(3):251-8.
Jenkins, et al. Management of gastroenteritis. Archives of Disease in Childhood. 1990; 65:939-941.
Martin, et al. A rapid and sensitive spectrophotometric method for the assay of chymotrypsin. Biol Chem. Feb. 1959;234(2):294-8.
Notice of Allowance dated Mar. 20, 2012 for U.S. Appl. No. 12/487,864.
Office Action dated Mar. 19, 2012 for U.S. Appl. No. 13/204,881.
Office Action dated Mar. 23, 2012 for U.S. Appl. No. 13/271,783.
Office Action dated Apr. 5, 2012 for U.S. Appl. No. 11/555,697.
Office Action dated Apr. 9, 2012 for U.S. Appl. No. 13/208,963.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Schumann. Medical, nutritional and technological properties of lactulose. An update. Eur J Nutr. Nov. 2002;41 Suppl 1:117-25.
Sillanaukee, et al. Improved diagnostic classification of alcohol abusers by combining carbohydrate-deficient transferrin and gamma-glutamyltransferase. Clin Chem. Apr. 2001;47(4):681-5.
U.S. Appl. No. 13/481,087, filed May 25, 2012, Fallon.
U.S. Appl. No. 13/502,989, filed Apr. 19, 2012, Heil et al.
U.S. Appl. No. 13/503,844, filed Apr. 24, 2012, Fallon et al.
Dajcs, et al. Lysostaphin is effective in treating methicillin-resistant *Staphylococcus aureus* endophthalmitis in the rabbit. Curr Eye Res. Jun. 2001;22(6):451-7.

Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Office action dated Jun. 13, 2012 for U.S. Appl. No. 12/493,122.
Dupiereux, et al. Creutzfeldt Jakob, Parkinson, lewy body dementia and Alzheimer diseases: from diagnosis to therapy. Cent Nery Syst Agents Med Chem. Mar. 2009;9(1):2-11.
Notice of allowance dated Jul. 3, 2012 for U.S. Appl. No. 13/271,783.
Office action dated Jun. 27, 2012 for U.S. Appl. No. 12/493,147.
Office action dated Jul. 11, 2012 for U.S. Appl. No. 12/573,353.
Office action dated Jul. 18, 2012 for U.S. Appl. No. 12/047,818.
Wisniewski, et al. Therapeutic approaches for prion and Alzheimer's diseases. FEBS J. Aug. 2007;274(15):3784-98. Epub Jul. 6, 2007.
U.S. Appl. No. 13/562,999, filed Jul. 31, 2012, Fallon.
U.S. Appl. No. 13/705,763, filed Dec. 5, 2012, Fallon et al.
Bowers. Endocrine secretions of the pancreas. Jul. 5, 2006. Accessed online at www.vivo.colostate.edu/hbooks/pathphys/digestion/pancreas/exocrine.html.
Office action dated Aug. 13, 2012 for U.S. Appl. No. 13/208,963.
Office action dated Sep. 13, 2012 for U.S. Appl. No. 13/481,087.
Office action dated Oct. 10, 2012 for U.S. Appl. No. 13/201,881.
Office action dated Oct. 25, 2012 for U.S. Appl. No. 13/144,286.
Office action dated Oct. 25, 2012 for U.S. Appl. No. 13/144,290.
Office action dated Dec. 6, 2012 for U.S. Appl. No. 13/002,136.
Walsh, et al. Reduced violent behavior following chemical therapy. Physiology and behavior. 2004; 82:835-839.
U.S. Appl. No. 13/407,408, filed Feb. 28, 2012, Fallon et al.
Office Action dated Mar. 5, 2012 for U.S. Appl. No. 12/535,676.
U.S. Appl. No. 13/733,873, filed Jan. 3, 2012, Fallon et al.
U.S. Appl. No. 13/737,225, filed Jan. 9, 2012, Fallon.
Bray, et al. Effect of dietary protein content on weight gain, energy expenditure, and body composition during overeating. A randomized controlled trial. JAMA. Jan. 4, 2012; 307(1):47-55.
Ferrone, et al. Pancreatic enzyme pharmacotherapy. Pharmacotherapy. 2007; 27:910-920.
Information of Papain from Worthington Enzymes webpage www.worthington-biochem.com/pap/default.html Downloaded Jan. 17, 2013.
International search report and written opinion dated Feb. 21, 2013 for PCT/US2013/020183.
International search report and written opinion dated Nov. 12, 2012 for PCT/US2012/034489.
Office action dated Jan. 22, 2013 for U.S. Appl. No. 13/562,999.
Office action dated Jan. 25, 2013 for U.S. Appl. No. 13/208,963.
Office action dated Feb. 14, 2013 for U.S. Appl. No. 13/193,346.
Office action dated Feb. 14, 2013 for U.S. Appl. No. 13/407,408.
Office action dated Feb. 21, 2013 for U.S. Appl. No. 12/047,818.
Olivar-Parra, et al. Training referential communicative skills to individuals with autism spectrum disorder: a pilot study. Psychological Reports. 2011; 109:921-939.
Patel, et al. Formulation and evaluation of mucoadhesive glipizide microspheres. AAPS PharmSciTech. 2005; 6(1):E49-E55.
Serna, et al. Pathogenesis and treatment of Shiga toxin-producing *Escherichia coli* infections. Curr Opin Gastroenterol. Jan. 2008;24(1):38-47.
Tamaro. Vitamin K deficiency as a cause of autistic symptoms. web.archive.org/web/20090612022246/http://www.gutresearch.com/VitaminK.pdf. Published Jun. 12, 2009 as per Wayback Engine.
U.S. Appl. No. 13/836,136, filed Mar. 15, 2013, Fallon et al.
Roxas, et al. Colds and influenza: a review of diagnosis and conventional, botanical, and nutritional considerations. Alternative Medicine Review. 2007; 12(1):25-48.
Millipore EMD catalog (online) Papain, unit definition, EMD Millipore Corp, 2013. Downloaded May 13, 2013.
UK search and examination report dated Mar. 26, 2013 for GB 1111565.6.
UK search and examination report dated Mar. 27, 2013 for GB 1111566.4.
UK search and examination report dated Apr. 18, 2013 for GB 1117669.0.

(56) References Cited

OTHER PUBLICATIONS

Office action dated May 9, 2013 for U.S. Appl. No. 13/204,881.
Office action dated May 15, 2013 for U.S. Appl. No. 13/502,989.
U.S. Appl. No. 13/926,822, filed Jun. 25, 2013, Fallon.
U.S. Appl. No. 14/007,793, filed Sep. 26, 2013, Fallon.
U.S. Appl. No. 14/037,652, filed Sep. 26, 2013, Fallon.
U.S. Appl. No. 14/037,696, filed Sep. 26, 2013, Fallon.
U.S. Appl. No. 14/087,930, filed Nov. 22, 2013, Fallon et al.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Carroccio, et al. Pancreatic enzyme therapy in childhood celiac disease. A double-blind prospective randomized study. Dig Dis Sci. Dec. 1995;40(12):2555-60.
Creon. Full prescribing information. Last edited Mar. 2013. Abbvie Inc 2012. www.rxabbvie.com/pdf/creon_PI.pdf.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
International search report and written opinion dated Aug. 27, 2013 for PCT/US2013/043444.
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Leeds, et al. Is exocrine pancreatic insufficiency in adult coeliac disease a cause of persisting symptoms? Aliment Pharmacol Ther. Feb. 1, 2007;25(3):265-71.
Notice of allowance dated Jan. 2, 2014 for U.S. Appl. No. 13/204,881.
Notice of Allowance dated May 29, 2013 for U.S. Appl. No. 13/481,087.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Oct. 29, 2013 for U.S. Appl. No. 13/204,881.
Office action dated Jan. 15, 2014 for U.S. Appl. No. 13/836,135.
Office action dated Jan. 16, 2014 for U.S. Appl. No. 12/046,252.
Office action dated Jan. 24, 2014 for U.S. Appl. No. 12/054,343.
Office action dated Jan. 24, 2014 for U.S. Appl. No. 12/786,739.
Office action dated Jun. 25, 2013 for U.S. Appl. No. 13/144,286.
Office action dated Jun. 25, 2013 for U.S. Appl. No. 13/144,290.
Office action dated Jul. 15, 2013 for U.S. Appl. No. 13/002,136.
Office action dated Jul. 31, 2013 for U.S. Appl. No. 13/757,412.
Office action dated Aug. 2, 2013 for U.S. Appl. No. 12/535,676.
Office action dated Aug. 14, 2013 for U.S. Appl. No. 13/448,061.
Office action dated Sep. 9, 2013 for U.S. Appl. No. 13/502,989.
Office action dated Oct. 24, 2013 for U.S. Appl. No. 13/313,708.
Office action dated Nov. 29, 2013 for U.S. Appl. No. 13/193,346.
Office action dated Dec. 10, 2013 for U.S. Appl. No. 13/407,408.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 16, 2013 for U.S. Appl. No. 12/535,676.
Okahata, et al. Lipid-coated enzymes as efficient catalysts in organic media. Trends in Biotechnology. 1997; 15(2):50-54.
Pancrease. Patient information leaflet. Pancrease HL Capsules. Last updated Apr. 30, 2013. Janssen-cilag LTD. www.medicines.org.uk/EMC/medicine/7326.
Petrolatum: Pharmaceutical Excipients. London: Pharmaceutical Press. 2006. 1-6.
Sienaert, et al. Evidence-based treatment strategies for treatment-resistant bipolar depression: a systematic review. Bipolar Disord. Feb. 2013;15(1):61-9. doi:10.1111/bdi.12026. Epub Nov. 27, 2012.
Xu. Pancreatin therapy in chronic pancreatitis. Clin J Dig, May 2005; 25(5):313-315. (in Chinese with English translation).
Digestive Enzyme Preparation: Pancreatin listed in Japanese Pharmacopoeia, Aug. 2008, <database.japic.or.jp/pdf/newPINS/00009938.pdf> (in Japanese with English translation).
Lebenthal, et al. Enzyme therapy for pancreatic insufficiency: present status and future needs. Pancreas. Jan. 1994;9(1):1-12.
MacDonald. Thyrotoxicosis treated with pancreatic extract and iodine. Lancet. 1943; 244(6251):788.
Office action dated Mar. 11, 2014 for U.S. Appl. No. 11/533,818.
U.S. Appl. No. 14/296,091, filed Jun. 4, 2014, Fallon.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Cichoke. Celiac disease. The complete book of enzyme therapy. Penguin. New York, NY. 1999; 174-177.
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Curemark press release. Curemark Receives Investigational New Drug Clearance For CM-AT for Autism. Mar. 26, 2009. www.medicalnewstoday.com/releases/143723.php.
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.
International preliminary report on patentability dated Jul. 17, 2014 for PCT/US2013/020183.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Notice of allowance dated Jun. 12, 2014 for U.S. Appl. No. 13/448,061.
Notice of allowance dated Aug. 11, 2014 for U.S. Appl. No. 13/193,346.
Notice of allowance dated Sep. 15, 2014 for U.S. Appl. No. 14/037,652.
Office action dated Apr. 10, 2014 for U.S. Appl. No. 13/502,989.
Office action dated Apr. 16, 2014 for U.S. Appl. No. 13/705,763.
Office action dated May 12, 2014 for U.S. Appl. No. 13/733,873.
Office action dated May 15, 2014 for U.S. Appl. No. 13/448,061.
Office action dated May 16, 2014 for U.S. Appl. No. 13/313,708.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 27, 2014 for U.S. Appl. No. 14/007,793.
Office action dated Jul. 7, 2014 for U.S. Appl. No. 12/535,676.
Office action dated Aug. 7, 2014 for U.S. Appl. No. 13/836,135.
Office action dated Aug. 29, 2014 for U.S. Appl. No. 13/144,286.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Pancreatin 8X USP Powder. Product Specification. Jul. 2000. In: Product Manual. American Laboratories Incorporated. Omaha, NE. p. 1.
Sundstrom, et al. A deadly prion disease: fatal familial insomnia. J Neurosci Nurs. Dec. 2003;35(6):300-5. Abstract only.
Williams, et al. Intravenous secretin for autism spectrum disorders (ASD). Cochrane Database Syst Rev. Apr. 18, 2012;4:CD003495. doi: 10.1002/14651858.CD003495.pub3.
U.S. Appl. No. 14/693,711, filed Apr. 22, 2015, Fallon.
U.S. Appl. No. 14/713,178, filed May 15, 2015, Fallon.
U.S. Appl. No. 14/713,221, filed May 15, 2015, Fallon et al.
U.S. Appl. No. 14/713,242, filed May 15, 2015, Fallon et al.
eMedExpert, Antibiotics:Cephalosporins, Available online at: www.emedexpert.com/compare/ cephalosporins.shtml, available as early as Jun. 2, 2007 per Internet Archive Wayback Machine.
Fliri, et al. Drug effects viewed from a signal transduction network perspective. J Med Chem. Dec. 24, 2009;52(24):8038-46. doi: 10.1021/jm901001p.
GM Chemie 2010 "Products: Hypromellose Phthalate" accessed from www.gmchemie.com on Sep. 22, 2014.

(56) References Cited

OTHER PUBLICATIONS

Merriam-Webster 2014 "Definition: Precipitate" accessed from www.mirriam-webster.com on Sep. 22, 2014.
Munasinghe et al. Digestive enzyme supplementation for autism spectrum disorders: a double-blind randomized controlled trial. J Autism Dev Disord. Sep. 2010;40(9):1131-8.
Nih, "Celiac Disease", National Digestive Diseases Information Clearinghouse: Bethesda, MD, 2008; 12 pages.
Notice of allowance dated Feb. 2, 2015 for U.S. Appl. No. 13/926,822.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Notice of allowance dated Dec. 23, 2014 for U.S. Appl. No. 14/007,793.
Office action dated Jan. 16, 2015 for U.S. Appl. No. 12/535,676.
Office action dated Mar. 6, 2015 for U.S. Appl. No. 13/757,412.
Office action dated Apr. 6, 2015 for U.S. Appl. No. 14/493,734.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office action dated Apr. 27, 2015 for U.S. Appl. No. 12/054,343.
Office action dated May 6, 2015 for U.S. Appl. No. 12/493,122.
Office action dated May 7, 2015 for U.S. Appl. No. 13/705,763.
Office action dated May 27, 2015 for U.S. Appl. No. 13/502,989.
Office action dated Jun. 3, 2015 for U.S. Appl. No. 13/002,136.
Office action dated Jul. 17, 2015 for U.S. Appl. No. 13/733,873.
Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office action dated Nov. 7, 2014 for U.S. Appl. No. 13/705,763.
Office action dated Nov. 21, 2014 for U.S. Appl. No. 13/926,822.
Office action dated Dec. 18, 2014 for U.S. Appl. No. 14/037,696.
Office action dated Dec. 19, 2014 for U.S. Appl. No. 13/733,873.
Richards, et al. Diagnosis, management, and treatment of Alzheimer disease: a guide for the internist. Arch Intern Med. Apr. 26, 1999;159(8):789-98.
Swayne, et al. Pathobiology of H5N2 Mexican avian influenza virus infections of chickens. Vet Pathol. Nov. 1997;34(6):557-67.
U.S. Appl. No. 14/921,896, filed Oct. 23, 2015, Fallon et al.
Borowitz, et al. Study of a novel pancreatic enzyme replacement therapy in pancreatic insufficient subjects with cystic fibrosis. J Pediatr. Nov. 2006;149(5):658-662.
Chazalette. A Double-Blind Placebo-Controlled Trial of a Pancreatic Enzyme Formulation (Panzytrat® 25 000) in the Treatment of Impaired Lipid Digestion in Patients with Cystic Fibrosis. Drug Investigation. May 1993; 5(5):274-280. Abstract only.
Creon digestive enzymes. Celic.com/ Jun. 2009. www.celiac.com/gluten-free/topic/59195-creon-digestive-enzymes.
Notice of allowance dated Nov. 16, 2015 for U.S. Appl. No. 14/493,734.
Notice of allowance dated Dec. 23, 2015 for U.S. Appl. No. 12/493,122.
Office action dated Oct. 30, 2015 for U.S. Appl. No. 14/528,715.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Dec. 10, 2015 for U.S. Appl. No. 13/836,135.
Office action dated Dec. 15, 2015 for U.S. Appl. No. 14/087,930.
Office action dated Dec. 18, 2015 for U.S. Appl. No. 14/640,385.
Office action dated Dec. 24, 2015 for U.S. Appl. No. 13/757,412.
Office action dated Dec. 24, 2015 for U.S. Appl. No. 14/612,580.
Shelby, et al. Enzymatic debridement with activated whole pancreas. American Journal of Surgery. Oct. 1958; 96(4):545-549.
Commentary on the Japanese Pharmacopoeia, 14th ed., D929-D931, 2001.
Office action dated Mar. 22, 2016 for U.S. Appl. No. 13/733,873.
Block, et al. A rapid food screener to assess fat and fruit and vegetable intake Am J Prev Med. May 2000;18(4):284-8.
Brinkley, et al. Factor analysis of the aberrant behavior checklist in individuals with autism spectrum disorders. J Autism Dev Disord. Nov. 2007;37(10):1949-59. Epub Dec. 21, 2006.
CDC, *Escherichia coli*, Travelers Health, Chapter 3: Infectious Diseases Related to Travel, Jul. 10, 2015, Available Online at: wwwnc.cdc.gov/tmvel/yellowbook/2016/infectious-diseases-related-to-travel/escherichia-coli.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
emc, Creon 10000 Capsules, May 18, 2015, Available Online at: www.medicines.org.uk/emc/medicine/2068.
Exocrine Pancreatic Insufficiency (Enzymes) Document downloaded online on Jan. 8, 2016 at: <www.epi4dogs.com/enzyme.htm>.
German, et al., Apple iPhone Review: Apple iPhone, Jun. 30, 2007; CINET.
Holquist, et al. FDA safety page: Delayed-release vs. extended-release Rxs; Jul. 23, 2007.
Holten, et al. Appropriate prescribing of oral beta-lactam antibiotics. Am Fam Physician. Aug. 1, 2000;62(3):611-20.
International search report and written opinion dated May 9, 2013 for PCT/US2013/024453.
Notice of allowance dated Mar. 1, 2016 for U.S. Appl. No. 14/087,930.
Notice of allowance dated Sep. 9, 2015 for U.S. Appl. No. 13/193,346.
Office action dated Jan. 15, 2016 for U.S. Appl. No. 13/502,989.
Office action dated Jan. 26, 2016 for U.S. Appl. No. 12/054,343.
Office action dated Jan. 29, 2016 for U.S. Appl. No. 12/786,739.
Office action dated Feb. 1, 2016 for U.S. Appl. No. 13/503,844.
Office action dated Feb. 17, 2016 for U.S. Appl. No. 14/713,178.
Office action dated Feb. 26, 2016 for U.S. Appl. No. 12/535,767.
Office action dated Mar. 2, 2016 for U.S. Appl. No. 14/693,711.
Office action dated Aug. 24, 2015 for U.S. Appl. No. 13/733,873.
Office action dated Aug. 31, 2015 for U.S. Appl. No. 12/535,676.
Office action dated Sep. 8, 2015 for U.S. Appl. No. 11/533,818.
Office action dated Sep. 11, 2015 for U.S. Appl. No. 13/313,708.
Regan, et al. Comparative effects of antacids, cimetidine and enteric coating on the therapeutic response to oral enzymes in severe pancreatic insufficiency. N Engl J Med. Oct. 20, 1977;297(16):854-8.
Schizophreniform disorder. Merck Manuals Online Medical Library. Nov. 2005. (in Japanese with English translation).
Seltzer, et al. The Symptoms of Autism Spectrum Disorders in Adolescence and Adulthood. Journal of Autism and Developmental Disorders. 2003; 33(6):565-581.
Skinner, et al. Treatment of Prion Disease with Heterologous Prion Proteins. PLoS One. Jul. 2, 2015;10(7):e0131993. doi: 10.1371/journal.pone.0131993. eCollection 2015.
We Move, PD Workbook, The WEMOVE Clinician's Guide to Parkinson's Disease, 2006.
Co-pending U.S. Appl. No. 15/265,415, filed Sep. 14, 2016.
Co-pending U.S. Appl. No. 15/354,940, filed Nov. 17, 2016.
U.S. Appl. No. 12/535,676 Office Action Mailed Sep. 13, 2016.
U.S. Appl. No. 14/612,580 Office Action Mailed Sep. 21, 2016.
U.S. Appl. No. 14/713,178 Final Office Action Mailed Oct. 14, 2016.
Anonymous: Emulsifiers for the preparation of active dry yeast, Research Disclosure, Mason Publications, Hampshire, GB, 236(6), Dec. 1983.
Brudnak, Mark et al., Guide to intestinal health in autism spectrum disorder, Kirkman Laboratories, (Oct. 2001).

(56) References Cited

OTHER PUBLICATIONS

Cichoke, AJ The Complete Book of Enzyme Therapy, Penguin (1999) pp. 206-208 and 38.
Co-pending U.S. Appl. No. 15/185,511, filed Jun. 17, 2016.
Co-pending U.S. Appl. No. 15/265,620, filed Sep. 14, 2016.
CREON—FDA Prescribing information side effects and uses. Revised Apr. 2015.
European Application No. 15 200616.9 Extended Search Report Mailed Jun. 22, 2016.
European Application No. 16150552.4-1455 Extended European Search Report Mailed Jun. 24, 2016.
Life Plus Somazyne accessed Jun. 10, 2016, Online at www.lifeplus.com/media/pdf/piSheets/US/ 6141-PI_EN.pdf.
Matikainen, et al. Autonomic dysfunction in long-standing alcoholism. Alcohol Alcohol. 1986;21(1):69-73. Abstract only.
Michael's Naturopathic Programs, Digestive Enzymes, Product #011161, Accessed on Jun. 10, 2016, online at: www.michaelshealth.com/retail/digestive-enzymes-659.html.
Notice of allowance dated Apr. 22, 2016 for U.S. Appl. No. 14/528,715.
Office action dated Mar. 30, 2016 for U.S. Appl. No. 14/296,091.
Office action dated Apr. 5, 2016 for U.S. Appl. No. 14/713,242.
Office action dated Apr. 6, 2016 for U.S. Appl. No. 13/313,708.
Office action dated Apr. 13, 2016 for U.S. Appl. No. 14/612,604.
Office Action Mailed May 11, 2016 U.S. Appl. No. 14/713,242.
Reeves, G. et al. Pharmacological Management of Attention-deficit hyperactivity disorder, Expert Opinion on Pharmacotherapy, 5(6):1313-1320. (Feb. 25, 2005).
Troy. Pancreatic Enzymes. Remington: The Science and Practice of Pharmacy, 21st edition. Lippincot Williams & Wilkins, 2006. p. 1304.
ULTRESA—FDA Prescribing Information Side Effects and Uses. Revised Sep. 2014.
U.S. Appl. No. 11/533,818 Final Office Action Mailed Jun. 7, 2016.
U.S. Appl. No. 12/054,343 Office Action Mailed Aug. 19, 2016.
U.S. Appl. No. 12/786,739 Office Action Mailed Sep. 20, 2016.
U.S. Appl. No. 13/002,136 Final Office Action Mailed Jun. 24, 2016.
U.S. Appl. No. 13/193,346 Notice of Allowability Mailed Jul. 14, 2016.
U.S. Appl. No. 13/193,346 Notice of Allowability Mailed Jun. 2, 2016.
U.S. Appl. No. 13/502,989 Notice of Allowance Mailed Aug. 10, 2016.
U.S. Appl. No. 13/503,844 Office Action Mailed Aug. 25, 2016.
U.S. Appl. No. 13/705,763 Final Office Action Mailed May 24, 2016.
U.S. Appl. No. 13/757,412 Final Office Action Mailed Jun. 30, 2016.
U.S. Appl. No. 13/836,135 Office Action Mailed Jul. 22, 2016.
U.S. Appl. No. 14/612,604 Notice of Allowance Mailed Jul. 20, 2016.
U.S. Appl. No. 14/639,425 Office Action Mailed Jul. 14, 2016.
U.S. Appl. No. 14/640,385 Supplemental Notice of Allowability Mailed May 26, 2016.
U.S. Appl. No. 14/713,221 Final Office Action Mailed Jun. 16, 2016.
VIOKACE—FDA Prescribing Information, Side Effects and Uses. Revised Mar. 2012.
Wolfson, D., Making sense of digestive enzymes, Klaire Labs, Mar. 13, 2006.
ZENPEP—FDA Prescribing Information, Side Effects and Uses. Revised Sep. 2014.
U.S. Appl. No. 14/713,242 Office Action Mailed Dec. 7, 2016.
U.S. Appl. No. 13/313,706 Notice of Allowance Mailed Dec. 15, 2016.
U.S. Appl. No. 14/693,711 Final Office Action Mailed Dec. 15, 2016.
U.S. Appl. No. 14/296,091 Final Office Action Mailed Jan. 3, 2017.
U.S. Appl. No. 14/713,178 Advisory Office Action Mailed Jan. 19, 2017.
U.S. Appl. No. 14/713,221 Non-Final Office Action Mailed Dec. 30, 2016.
Button, KS et al. Power failure: why small sample size undermines the reliability of neuroscience. Nat. Rev. Neurosci. 14:365376 (2013).
Riedel, L et al. Limitations of faecal chymotrypsin as a screening test for chronic pancreatitis. Gut, 32:321-324 (1991).

\* cited by examiner

METHOD FOR TREATING PERVASIVE DEVELOPMENT DISORDERS

CROSS-REFERENCE TO RELATED APPLICATION

This application is a Divisional of U.S. application Ser. No. 12/283,090, filed Sep. 8, 2008, which is a Continuation of U.S. application Ser. No. 10/681,018, filed Oct. 8, 2003, which is a Continuation of U.S. application Ser. No. 09/707,395, filed on Nov. 7, 2000, now U.S. Pat. No. 6,632,429, which is a Continuation-in-part of U.S. application Ser. No. 09/466,559, filed on Dec. 17, 1999, now U.S. Pat. No. 6,534,063, which are incorporated by reference as if set forth in full herein.

BACKGROUND

1. Technical Field

The present invention relates generally to a method for treating individuals diagnosed with a form of PDD (pervasive development disorder) and other disorders such as ADD (attention deficit disorder) and ADHD (attention deficit hyperactivity disorder). More specifically, the present invention is directed to therapeutic method for treating individuals with such disorders by administering secretin, other neuropeptides, peptides, and/or digestive enzymes, as well as a prognosticative method for determining the potential effectiveness of the administration of secretin, other neuropeptides, peptides, and/or digestive enzymes for the treatment of such disorders.

2. Description of Related Art

PDDs are a class of disorders defined by both American and International diagnostic systems (i.e., the Diagnostic and Statistical Manual of Mental Disorders, 4th edition (DSM-IV) and World Health Organization: International Classification of Diseases, Tenth revision (ICD-10)). The spectrum of PDDs includes disorders such as Autism, Aspergers, ADD, and ADHD. PDDs are typically characterized by multiple distortions in the development of basic psychological functions that are involved in the development of social skills and language, such as attention, perception reality testing and motor movement. In addition, many children diagnosed with Autism, for example, suffer from primary diffuse gastrointestinal problems such as protracted diarrhea and constipation. Although PDDs are currently of unknown etiology, many conventional methods, such as dietary alteration, behavioral modification, and medication, have been utilized for treating individuals suffering from PDD related disorders. Unfortunately, PDD related disorders have no known treatment beyond that which is symptomatic, and these conventional methods have proven unsuccessful in allowing such children and adults to become symptom, or disorder free.

A child which displays signs of developmentally inappropriate inattention, impulsivity and hyperactivity is typically diagnosed as having ADD and/or ADHD. With these disorders, there can be marked disturbances of organization, distractibility, impulsivity, restlessness, and other disturbances of language and/or social behavior. A combination of psychiatric care and medicine is typically used for treating children with ADD and ADHD.

It was recently discovered that the administration of secretin, a gastrointestinal peptide hormone, to children diagnosed with Autism resulted in ameliorating the symptoms associated with Autism. This finding was published in the article by Horvath et al., entitled *Improved Social and Language Skills After Secretin Administration In Patients with Autistic Spectrum Disorders*, Journal of the Association for Academic Minority Physician Vol. 9 No. 1, pp. 9-15, January, 1998. The secretin administration, as described in Horvath, was performed as a diagnostic procedure, i.e., to stimulate pancreaticaobiliary secretion during an upper gastrointestinal endoscopy, rather than as a therapeutic procedure. Although the specific mechanism by which the secretin improved the autistic-related symptoms was not specifically identified, Horvath postulated that secretin may have had a direct or indirect effect on the central nervous system. What is important, however, is that this was the first time that gastrointestinal problems of autistic children were linked to a possible etiology in Autism.

Accordingly, in view of such findings, a method for determining whether an individual suffering from a disorder in the PDD spectrum will benefit from the administration of secretin, other neuropeptides, peptides and/or digestive enzymes, as well as a therapeutic method for treating such individuals with the administration of secretin, other neuropeptides, peptides arid/or digestive enzymes, are highly desired.

SUMMARY OF THE INVENTION

The present invention is directed to a method of analyzing the chymotrypsin level of an individual to determine the potential benefit of the administration of secretin, other neuropeptides, peptides and/or digestive enzyme administration to such individual, and in particular, as a prognosticative of potential secretin, other neuropeptides, peptides, and/or digestive enzyme administration for individuals diagnosed as having ADD, ADHD, Autism and other PDD related disorders.

In one aspect, a method for determining the efficacy of secretin, other neuropeptides, peptides, or digestive enzymes for the treatment of an individual diagnosed with a pervasive developmental disorder (PDD) comprises obtaining a sample of feces from an individual, determining a quantitative level of chymotrypsin present in the sample, and correlating the quantitative level of chymotrypsin determined to be present in the sample with the PDD to determine the efficacy of treating the individual with secretin, other neuropeptides, peptides, or digestive enzyme administration.

In another aspect, a therapeutic method for treating an individual diagnosed with a PDD pervasive developmental disorder comprises determining the efficacy of the administration of secretin, other neuropeptides, peptides, and digestive enzyme for the treatment of the individual based on a measure of the individual's chymotrypsin level, and administering secretin, other neuropeptides, peptides, or digestive enzymes to the individual based on the determination of the measure of the individual's chymotrypsin level.

The present invention involves determining the presence of abnormal protein digestion of individuals, especially children, by measuring the chymotrypsin levels so as to determine if the individual is likely to benefit from the administration of secretin, digestive enzymes, peptides and/or neuropeptides. Although there have been methods to test fecal samples for indications of cystic fibrosis and pancreatic diseases in infants, none of the known methods have tested fecal samples in determining the benefits of administering secretin, other neuropeptides, peptides and/or digestive enzymes to individuals suffering from a PDD. Indeed, insofar as an individual's fecal chymotrypsin level is a broad measure of protein and fat digestion, such levels can be applied to all those who may benefit from improvements in this mode of digestion. Furthermore, as low measures of fecal chymotrypsin expresses an abnormality of protein digestion, it is postulated that an improvement of protein digestion to promote normal growth and development of an individual suffering from a PDD by the administration of secretin, other neuropeptides, peptides and/or digestive enzymes, can ameliorate the symptomatologies of PDDs.

Accordingly, in another aspect of the present invention, a therapeutic method is provided for treating an individual diagnosed with a PDD including but not limited to Autism, Aspergers, ADD and ADHD, comprising the steps of:

determining the effectiveness of secretin administration for the treatment of the individual based on a measure of the individual's chymotrypsin level; and administering secretin therapy to the individual based on the determination of the measure of the individual's chymotrypsin level.

In yet another aspect, the therapeutic method involves administering a fecal chymotrypsin test to measure an individual's fecal chymotrypsin level. Preferably, an enzymatic spectrophotometry method is used for measuring the fecal chymotrypsin level of the individual. Upon determinating that an individual has an abnormal level of chymotrypsin, the individual is preferably administered 1 U/kg of body weight of porcine or human secretin by means of an intravenous push method. This method can be described as the administration of an IV push of saline solution and secretin to equal 1 U/kg of body weight. The individual then receives 1 unit test dose (absolute). A period of one minute is allowed to pass to determine if the individual has any allergic reactions to the secretin. After one minute has elapsed, if no urticarial reaction or any other allergic reaction has occurred, the remainder of the dose is administered. Subsequent fecal chymotrypsin samples are then gathered at one week intervals post administration to determine any changes in the chymotrypsin levels.

These and other aspects, features and advantages of the present invention will be described and become apparent from the following detailed description of preferred embodiments, which is to be read in connection with the accompanying drawings.

DETAILED DESCRIPTION OF PREFERRED EMBODIMENTS

Figure 1:
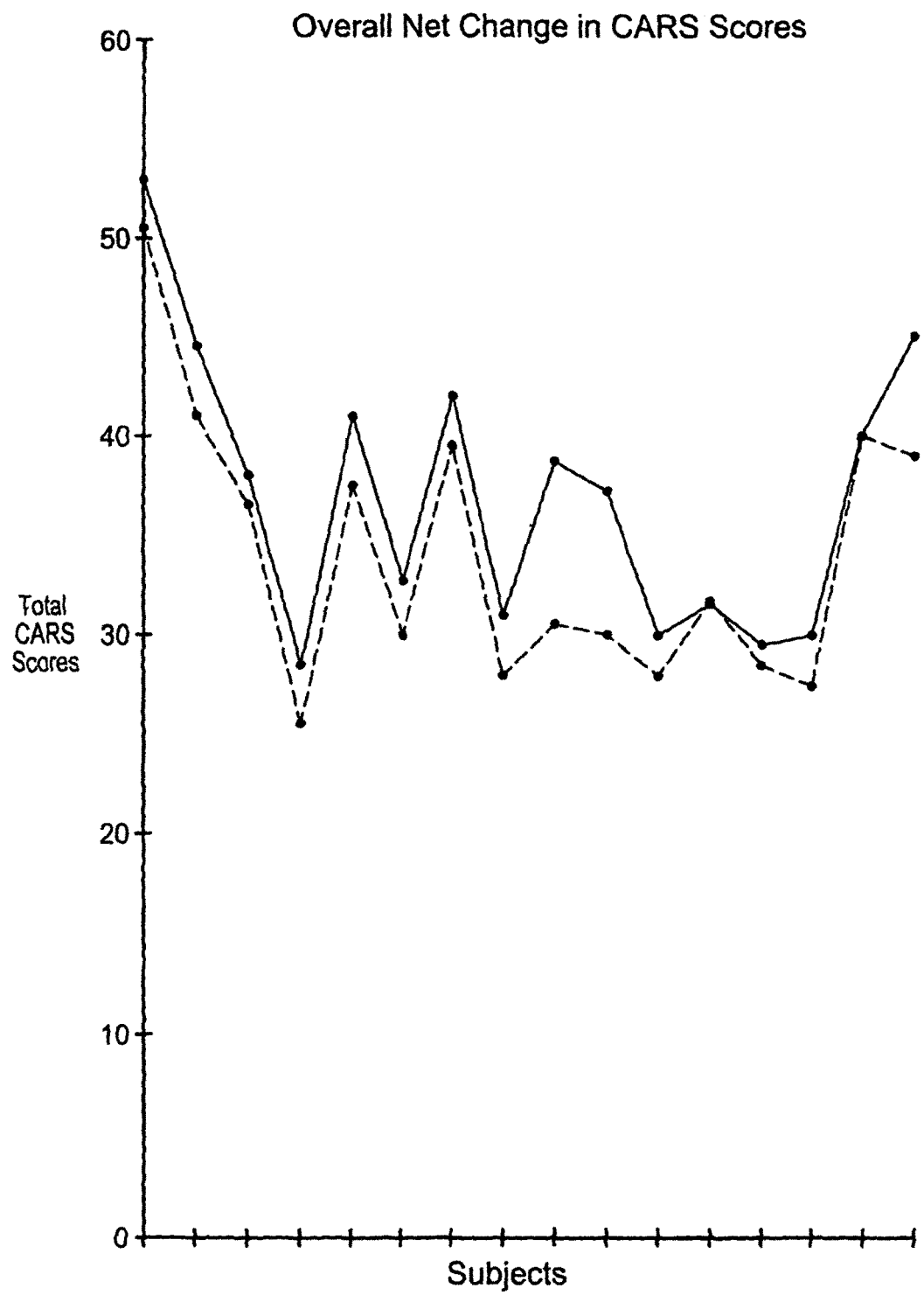
FIG. 1 illustrates the overall net change in results of a CARS test (Childhood Autism Rating Scale) depicting behavior of 16 autistic children pre-secretin and post-secretin administration, where the solid lines indicate pre-secretin scores and the dotted lines indicate post-secretin scores.

The present invention is directed to a method of analyzing chymotrypsin levels in persons, especially children, as a measure of the success of administering secretin, other neuropeptides, peptides and/or digestive enzymes for the therapeutic treatment of ADD, ADHD, Autism, Aspergers and other PDD related disorders. The use of secretin for the treatment of Autism is presently in the investigational stages. When the positive affects of the neuropeptide secretin on childhood autism were first discovered and published, research was conducted by the present inventor to formulate a process that would enable one to definitively determine if individuals, especially children, having a PDD could be tested prior to the administration of secretin for its possible efficacy for treating PDD. Tests were performed to measure the fecal chymotrypsin levels (referred to herein as Fecal Chymotrypsin Test) in children who span the entire PDD spectrum and whose symptomotology place them in this DSM IV category. As demonstrated below, such tests revealed that a majority of the children diagnosed with autism, ADD and ADHD, for example, had abnormal chymotrypsin levels. It is believed that such abnormal levels of chymotrypsin have not heretofore been identified in the PDD population of children and adults.

It is postulated that the abnormal levels of chymotrypsin are due to the inability of the pancreas to release bicarbonate ions, due to the lack of secretin mechanization in the small intestines. The small intestine has a pH in the range of 1.0-1.5 when the bolus of food enters the small intestines. Normally, plasma concentrations of secretin increase when the duodenal pH is below 4.5, and typically doubles during the postprandial period. The s cells in the proximal portion of the small intestines release secretin in response to this low pH. The secretin is then released into the bloodstream and ultimately reaches the pancreas. In response, the pancreas releases bicarbonate ions, water and electrolytes into the small intestines thus neutralizing the pH by bringing it from a 1.0-1.5 to approximately 6.5.

Following this, the pancreas secretes the enzyme trypsin in an inactive form trypsinogen. The trypsinogen is converted to trypsin in the small intestines. In an environment where the pH is 6.5 or greater, the trypsin catalyzes the formation of chymotrypsinogen to chymotrypsin. These enzymes are essential for the digestion of protein. In the absence of protein digestion, the amino acids necessary for the growth and development of individuals are absent. Therefore, based on tests performed by the present inventor, it is postulated that the increase of protein digestion of an individual suffering from PDD can lead to the improvement of such disorders. Accordingly, since secretin is responsible for aiding in the protein digestion process, it has been determined that the presence of abnormal protein digestion in individuals, especially children, is indicative of which individuals are likely to benefit from the administration of secretin.

Indeed, in accordance with the present invention, experimental results have shown that the potential benefit of administering secretin, other neuropeptides, peptides and/or digestive enzymes to individuals diagnosed with developmental disorders falling within the entire spectrum of PDD may be predetermined by analyzing the measured fecal chymotrypsin levels of such individuals. More specifically, as illustrated below, it has been determined that sub-normal to abnormal levels of fecal chymotrypsin in children/adults with PDD symptoms will benefit from the administration of secretin, other neuropeptides, peptides and/or digestive enzymes. In addition, experimental tests by the present inventor have revealed that the administration of secretin, other neuropeptides, peptides and/or digestive enzymes to others beyond those of who are autistic, especially those diagnosed with ADD and ADHD will benefit from the administration of secretin, other neuropeptides, peptides and/or digestive enzymes.

The following experiments describe exemplary diagnosis and treatment procedures in accordance with the invention. It is to be understood that these experiments and corresponding results are set forth by way of illustration only, and nothing therein shall be construed as a limitation on the overall scope of the invention.

Experiment 1

Figure 13:
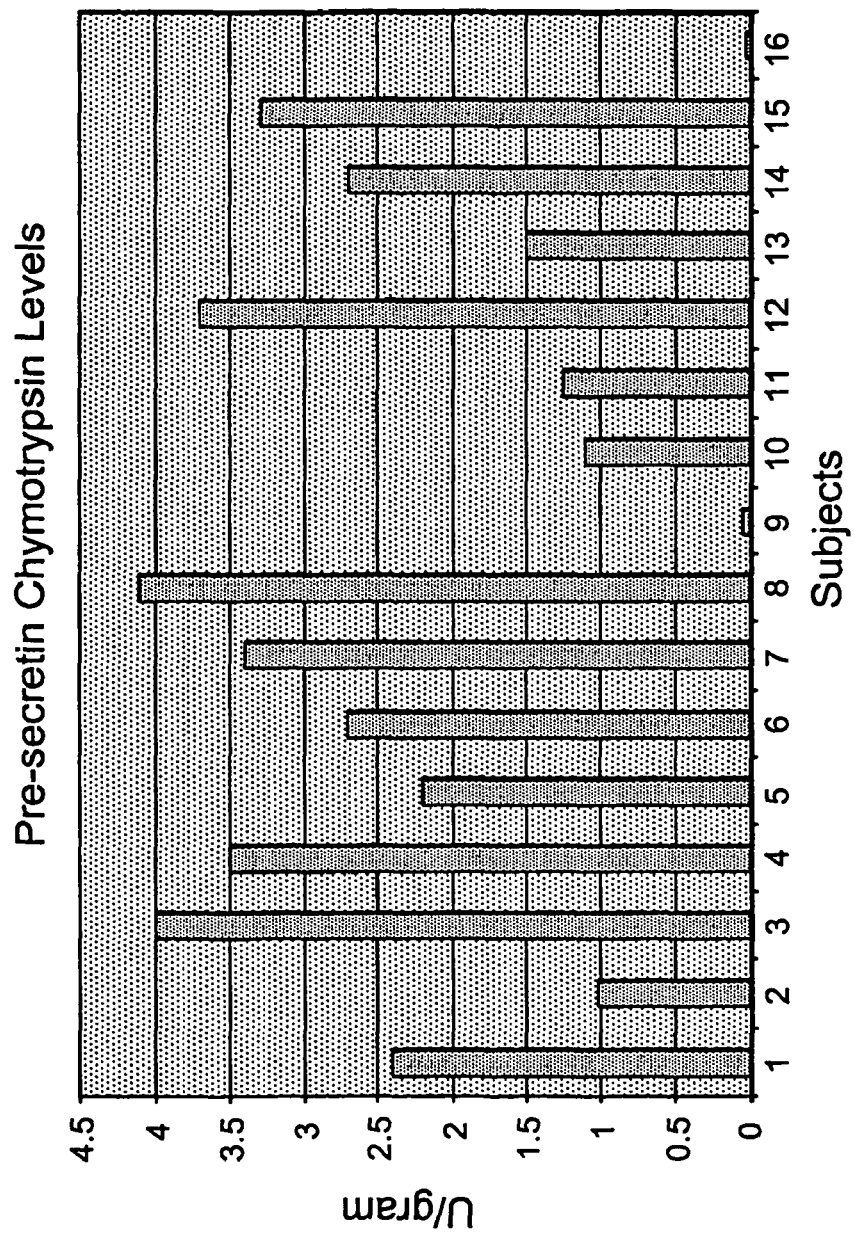
FIG. 13 illustrates the measured fecal chymotrypsin levels of 16 autistic children pre-secretin administration.

In this experiment, 16 children diagnosed as having autism were administered the following Fecal Chymotrypsin Test in accordance with an embodiment of the invention. First, approximately 2 grams of stool were collected from each child and placed in a sterile container (although it is to be understood that any quantity of stool may be collected, as 2 grams of stool is not a required amount). Each stool sample was then analyzed using, e.g., an enzymatic photo spectrometry analysis as is known by those skilled in the art, to determine the level of fecal chymotrypsin in the stool. Although the enzymatic photospectrophotometry process is preferred, any suitable conventional method may be used for measuring the fecal chymotrypsin levels. The measured chymotrypsin levels of the 16 autistic children are illustrated in FIG. 13.

After determining the chymotrypsin levels of the stools, each of these levels were compared with threshold chymotrypsin levels to determine if the child was likely to benefit from secretin administration. By way of example, with the fecal chymotrypsin tests of the stool samples being performed at 30° C., normal levels of chymotrypsin are deemed to lie above 8.4 U/gram, whereas pathologically abnormal levels are deemed to lie below 4.2 U/gram. In addition, chymotrypsin levels between 8.4 U/gram and 4.2 U/gram are considered equivocal, and further testing of the individual's fecal chymotrypsin levels over a period of time should be performed. It is to be noted that as shown in FIG. 13, all of the 16 autistic children that were tested had abnormal levels of fecal chymotrypsin pre-secretin administration.

Another stool sample was then collected from each child two days after the first test and analyzed to determine the chymotrypsin levels. This second test is preferably performed to obtain additional chymotrypsin measurements to make a more accurate determination. Those children having abnormal levels of chymotrypsin in their stools are considered candidates for secretin administration. Other factors that may be considered in determining which children are potential candidates for secretin administration aside from the fecal chymotrypsin levels include a previously diagnosed history of autism, a history of gastrointestinal (GI) dysfunction, including any history of protracted diarrhea or constipation lasting for a weeks or months, as well as a self-limiting diet consisting primarily of carbohydrates.

Upon determining that a given child was likely to benefit from secretin administration based on the results of the fecal chymotrypsin test, the child was administered a CARS (Childhood Autism Rating Scale) test prior to being scheduled for secretin infusion.

For each of the 16 autistic children tested, a preferred secretin infusion process according to the present invention was performed involving the administering of 1 U/kg of body weight of Secretin-Ferring for a period of nine months at intervals of approximately 6 weeks. In addition, another CARS test was administered to each of the 16 autistic children 3 weeks post secretin administration to determine if their autism had changed post infusion.

A preferred secretin infusion process includes the initial step of prepping an arm of the candidate child with an IV injection of saline. A test dose of 1 U of Secretin-Ferring is then administered to the child. Approximately one minute after infusion, the child is examined for signs of allergic reaction including rash, increased heart rate, and increase of blood pressure. If the child does not display any signs of allergic reaction, the remaining units of Secretin-Ferring is administered to the child in the manner of an IV push, which is then followed by a saline flush. Subsequently, each child receives a 1 U/kg of body weight infusion of Secretin-Ferring approximately every 6 weeks for 9 months. It is to be understood that any commercially available form of secretin may be used.

Results of Experiment 1

Figure 14:
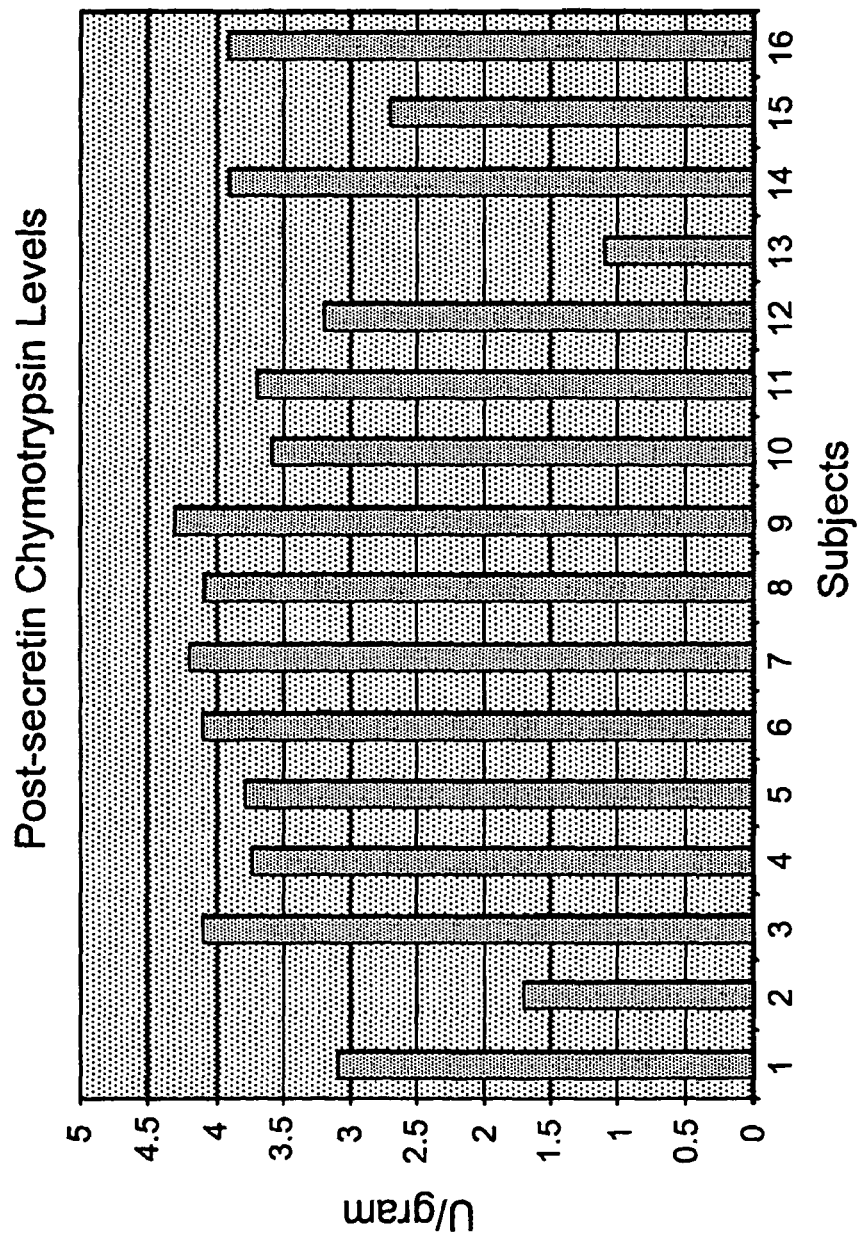
FIG. 14 illustrates the measured fecal chymotrypsin levels of the 16 autistic children approximately one week post-secretin administration.

The results of Experiment 1 are illustrated in FIGS. 1-14. For instance, approximately one week after the first secretin infusion, the fecal chymotrypsin level of each of the 16 autistic children was measured again. The results of this test are illustrated in FIG. 14. As shown, the chymotrypsin level of each of the 16 autistic children test increased post-secretin administration (as compared with the levels shown in FIG. 13).

Figure 2:
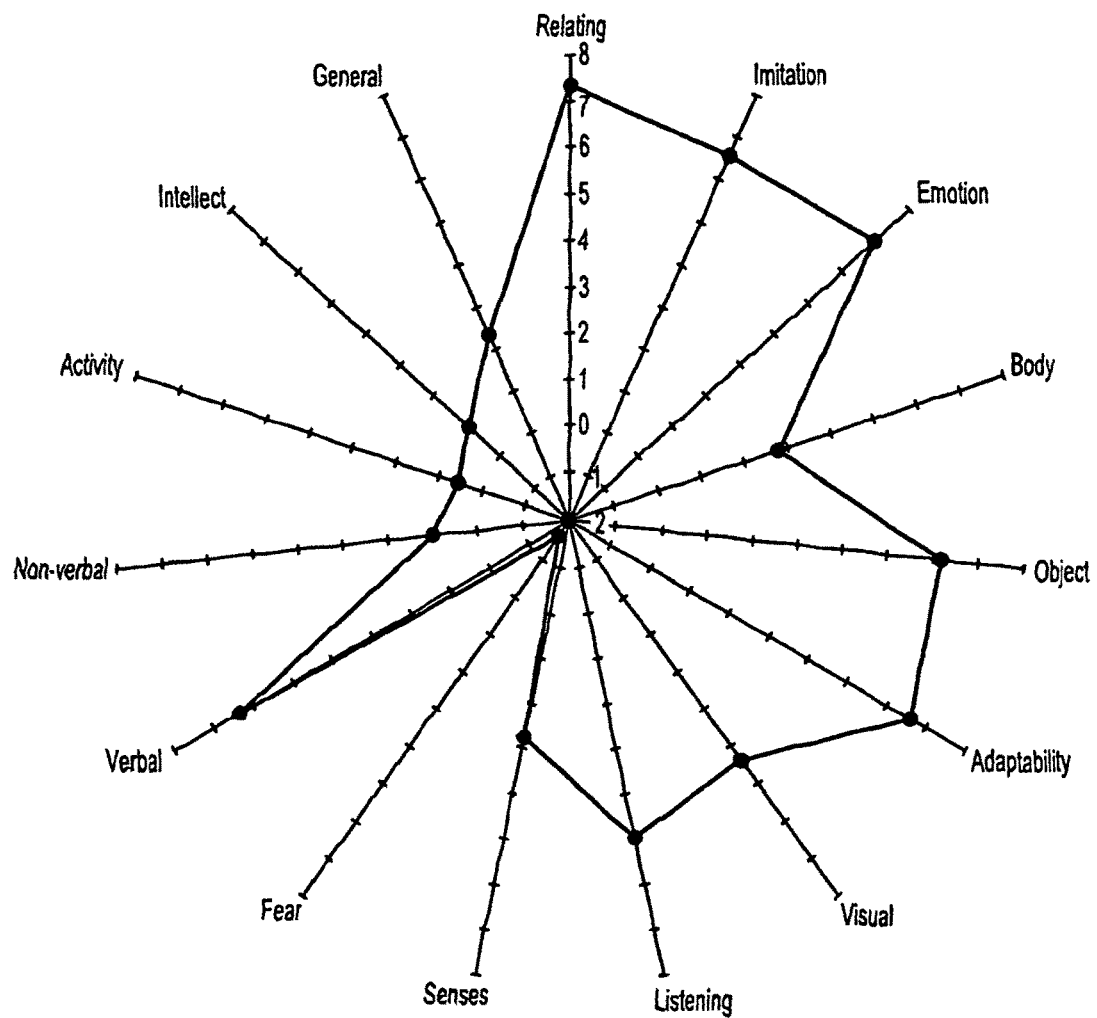
FIG. 2 illustrates percentage change from pre-secretin to post-secretin administration in the average scores of the respective components of the CARS test of FIG. 1.
Figure 3:
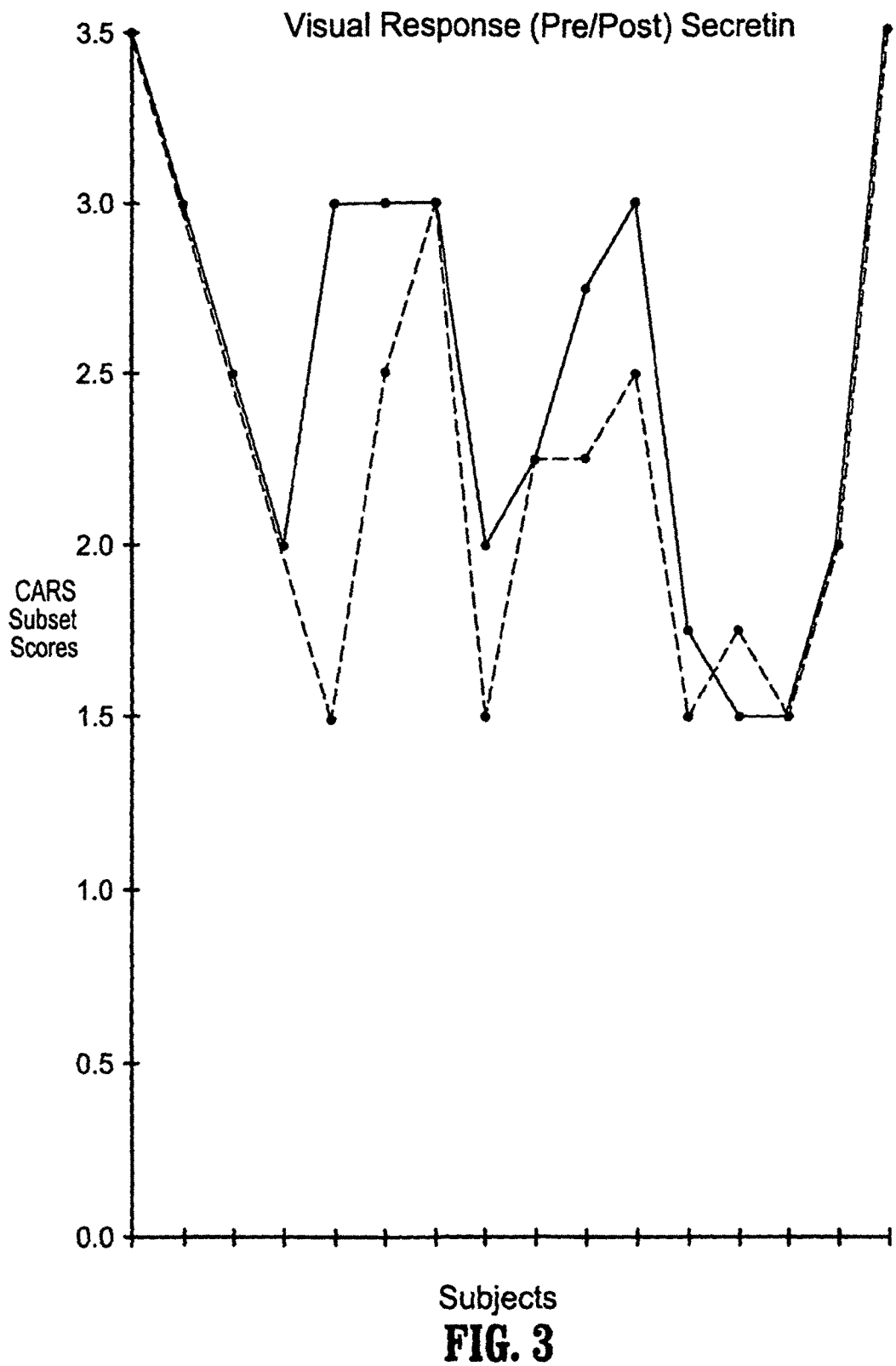
FIG. 3 illustrates the change in CARS scores for the sub-class Visual response from pre-secretin administration to three weeks post-secretin administration, where the solid lines indicate pre-secretin scores and the dotted lines indicate post-secretin scores.
Figure 4:
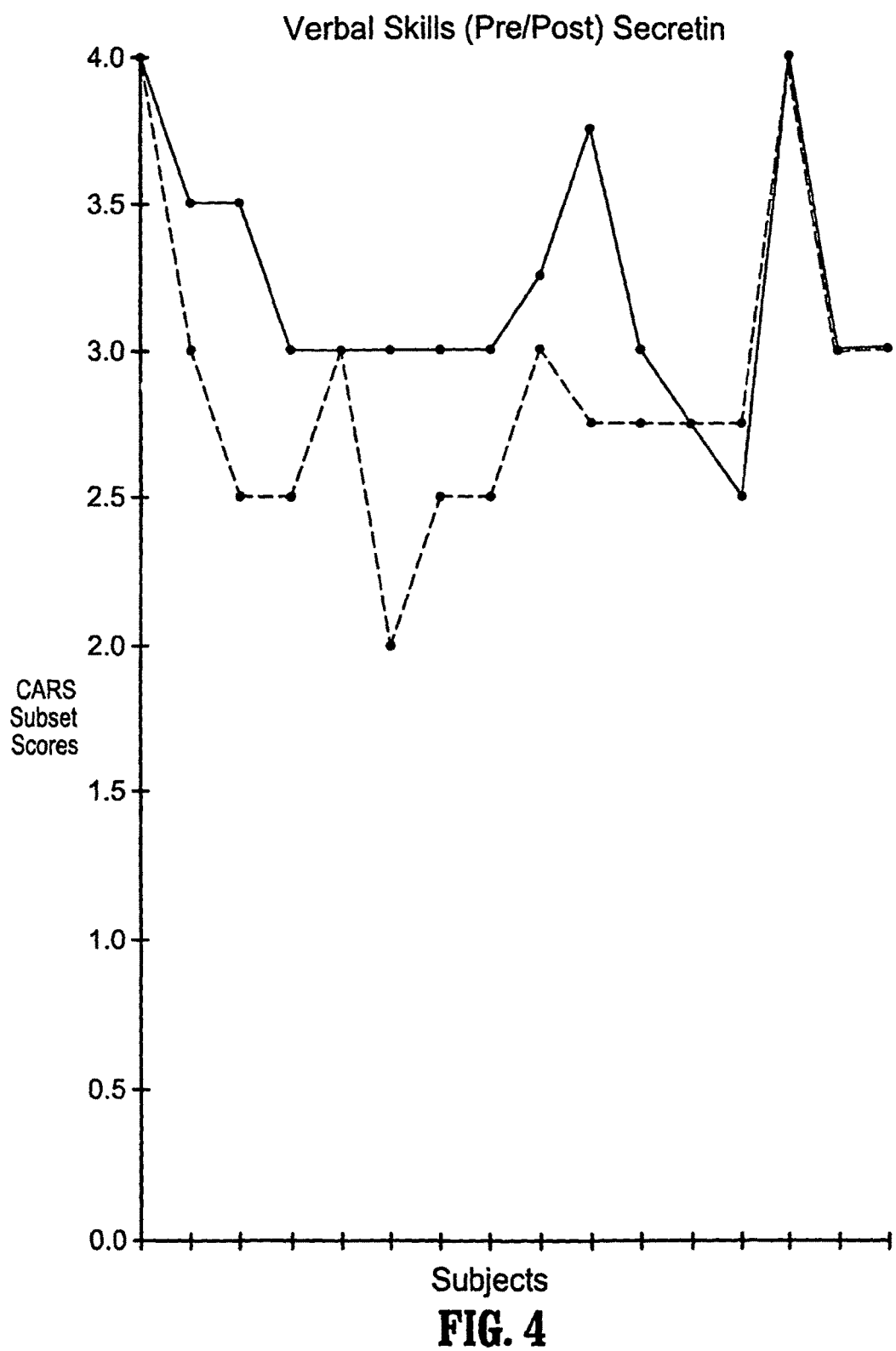
FIG. 4 illustrates the change in CARS scores for the sub-class Verbal Skills from pre-secretin administration to three weeks post-secretin administration, where the solid lines indicate pre-secretin scores and the dotted lines indicate post-secretin scores.
Figure 5:
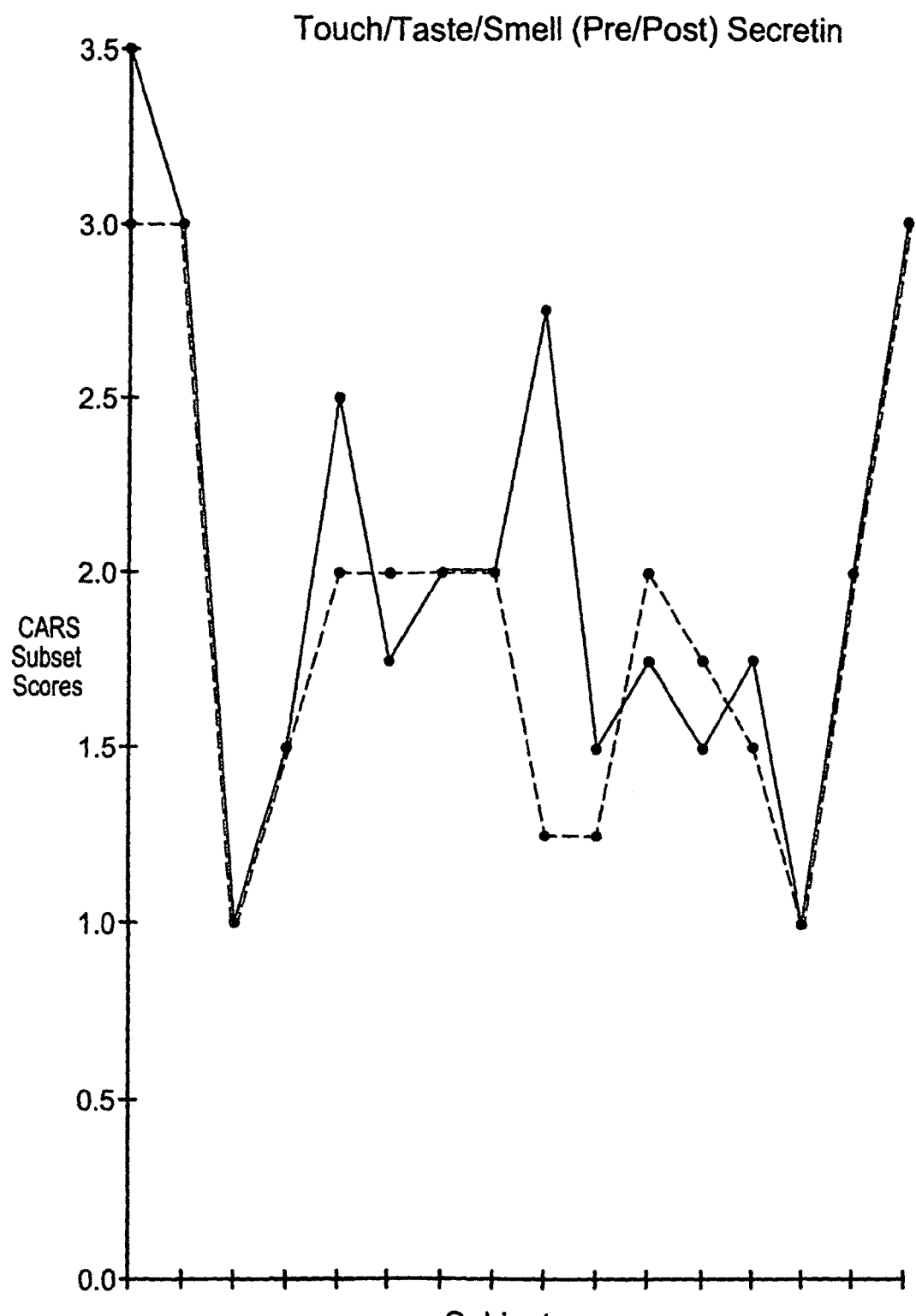
FIG. 5 illustrates the change in CARS scores for the sub-class Touch/Taste/Smell from pre-secretin administration to three weeks post-secretin administration, where the solid lines indicate pre-secretin scores and the dotted lines indicate post-secretin scores.
Figure 6:
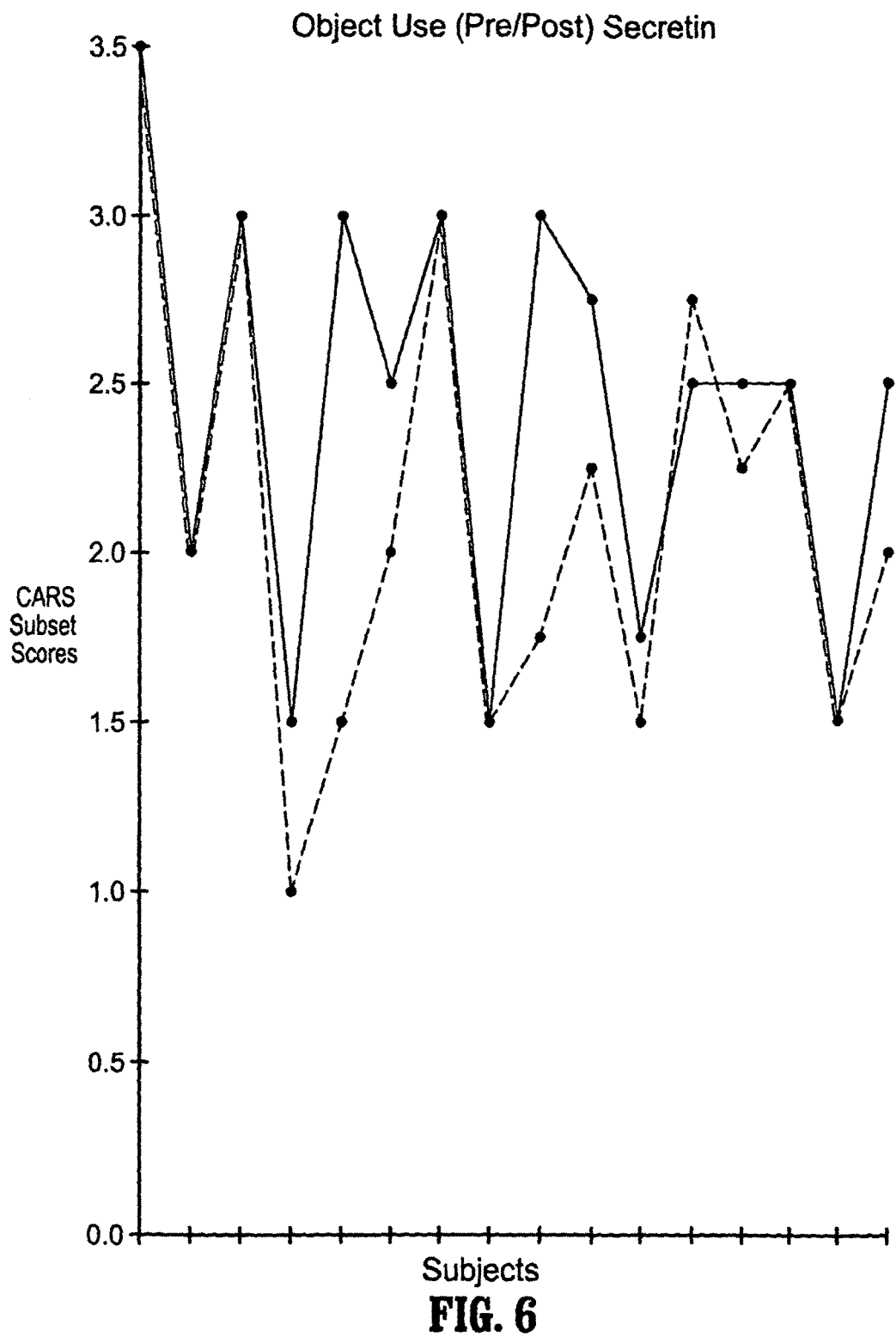
FIG. 6 illustrates the change in CARS scores for the sub-class Object Use from pre-secretin administration to three weeks post-secretin administration, where the solid lines indicate pre-secretin scores and the dotted lines indicate post-secretin scores.
Figure 7:
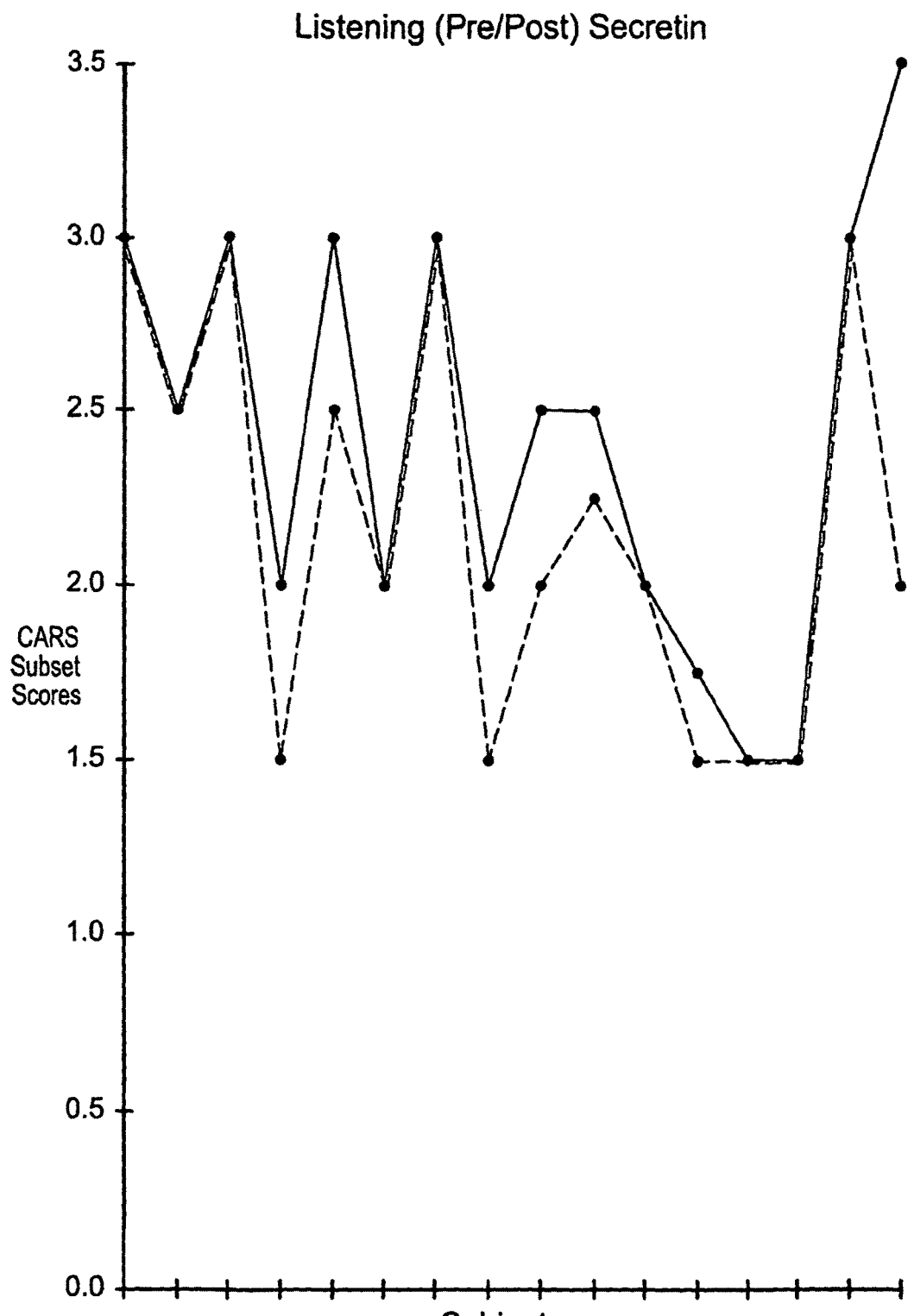
FIG. 7 illustrates the change in CARS scores for the sub-class Listening from pre-secretin administration to three weeks post-secretin administration, where the solid lines indicate pre-secretin scores and the dotted lines indicate post-secretin scores.
Figure 8:
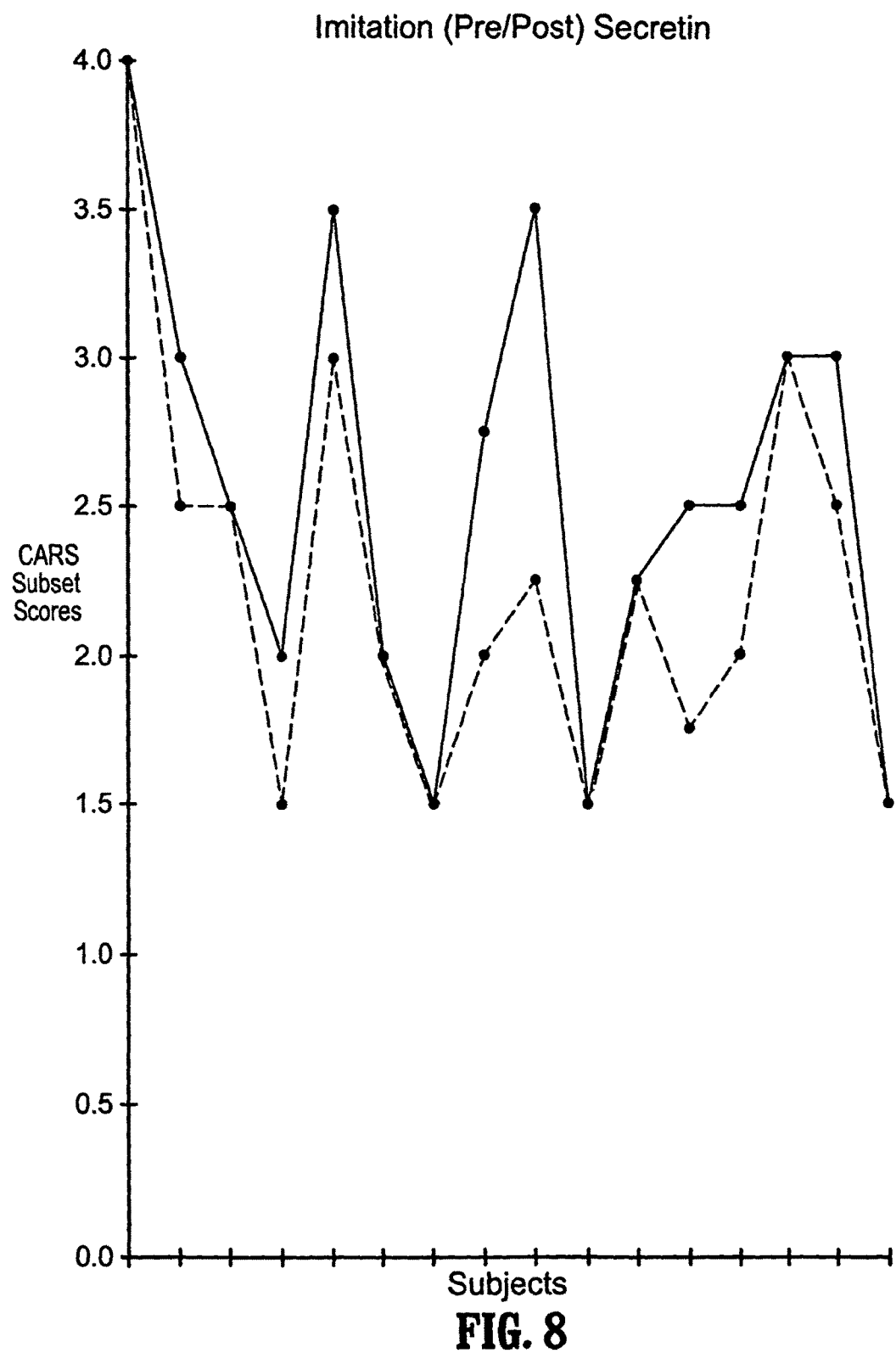
FIG. 8 illustrates the change in CARS scores for the sub-class Imitation from pre-secretin administration to three weeks post-secretin administration, where the solid lines indicate pre-secretin scores and the dotted lines indicate post-secretin scores.
Figure 9:
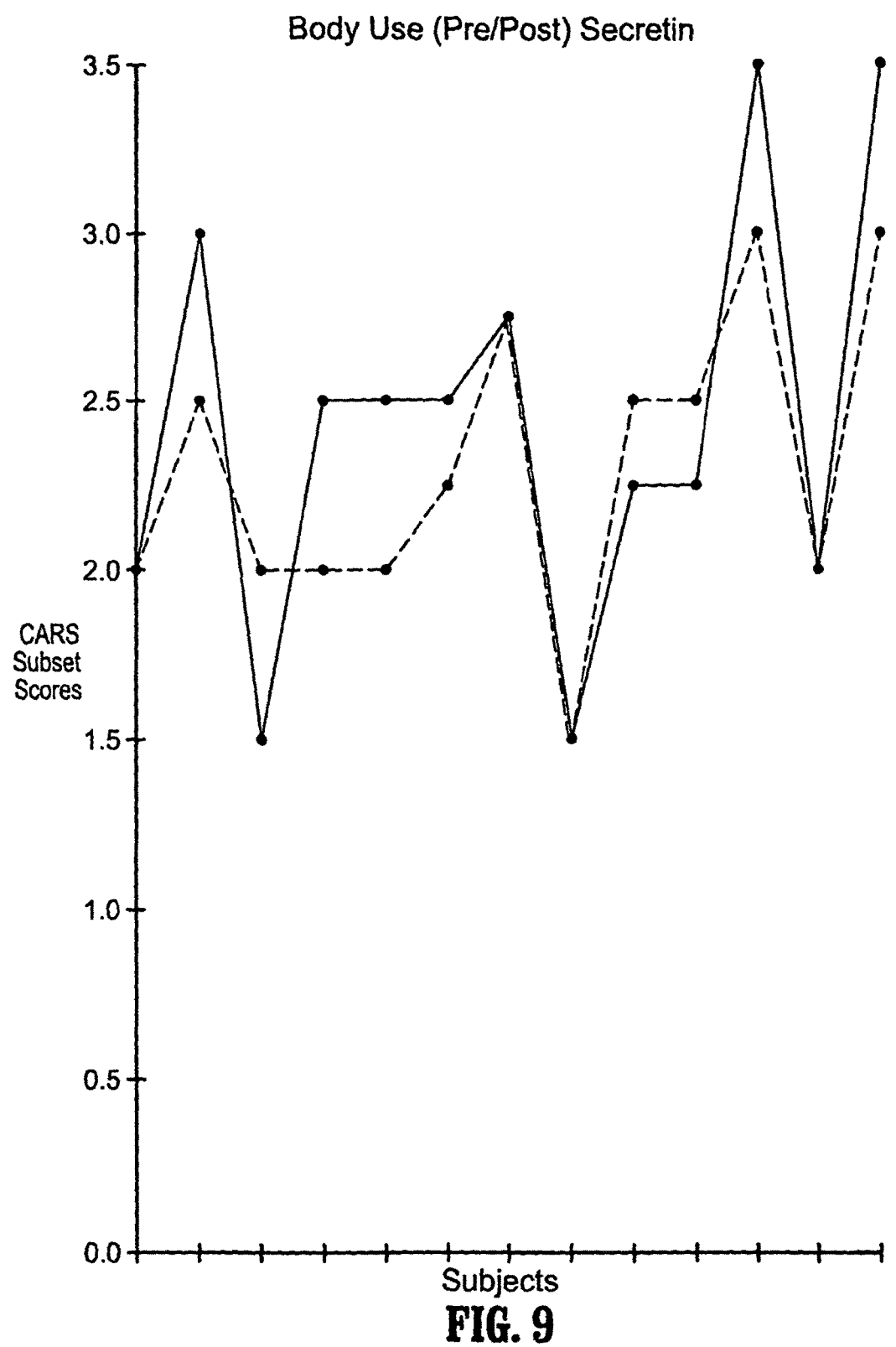
FIG. 9 illustrates the change in CARS scores for the sub-class Body Use from pre-secretin administration to three weeks post-secretin administration, where the solid lines indicate pre-secretin scores and the dotted lines indicate post-secretin scores.
Figure 10:
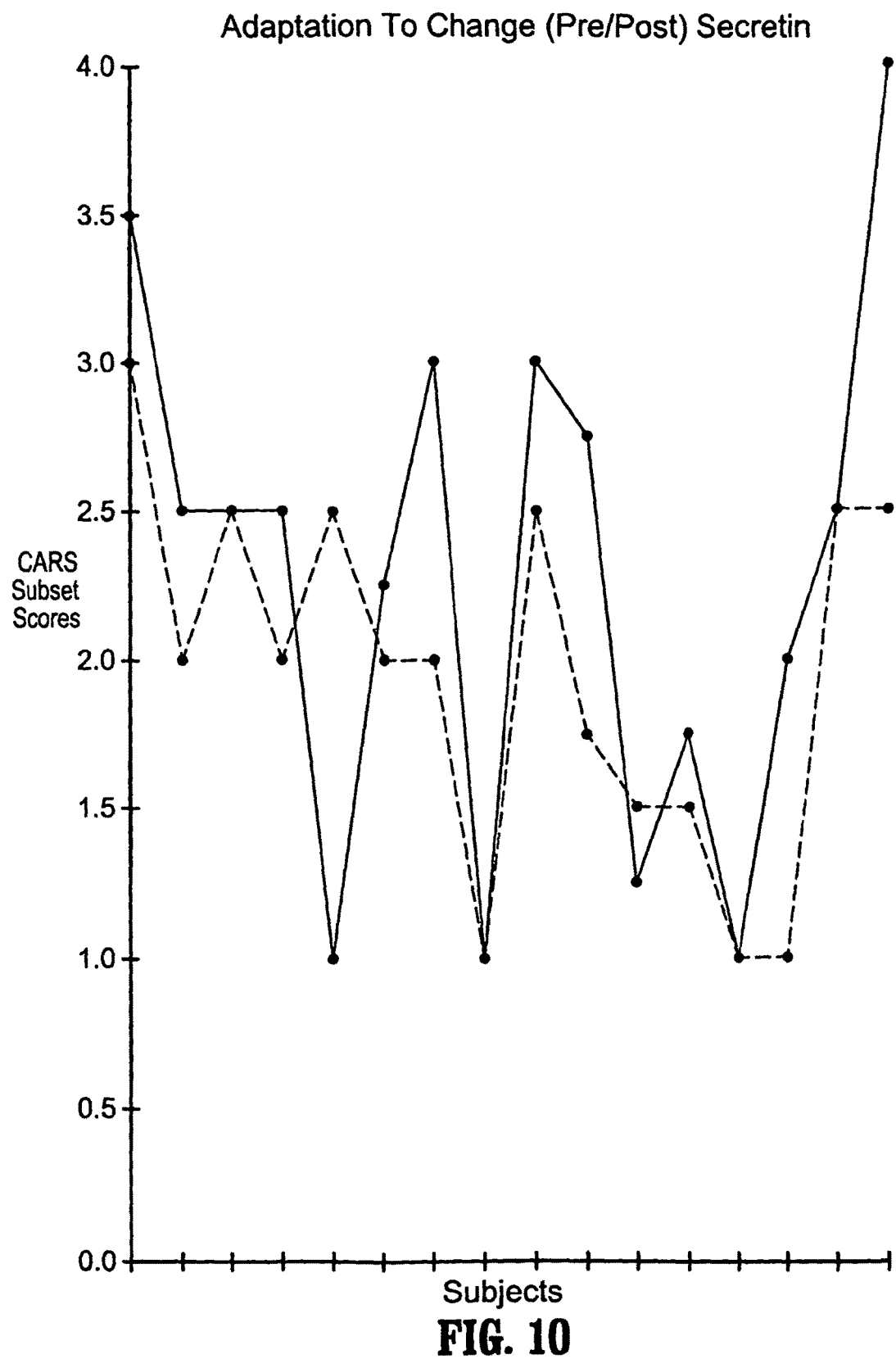
FIG. 10 illustrates the change in CARS scores for the sub-class Adaptation to Change from pre-secretin administration to three weeks post-secretin administration, where the solid lines indicate pre-secretin scores and the dotted lines indicate post-secretin scores.
Figure 11:
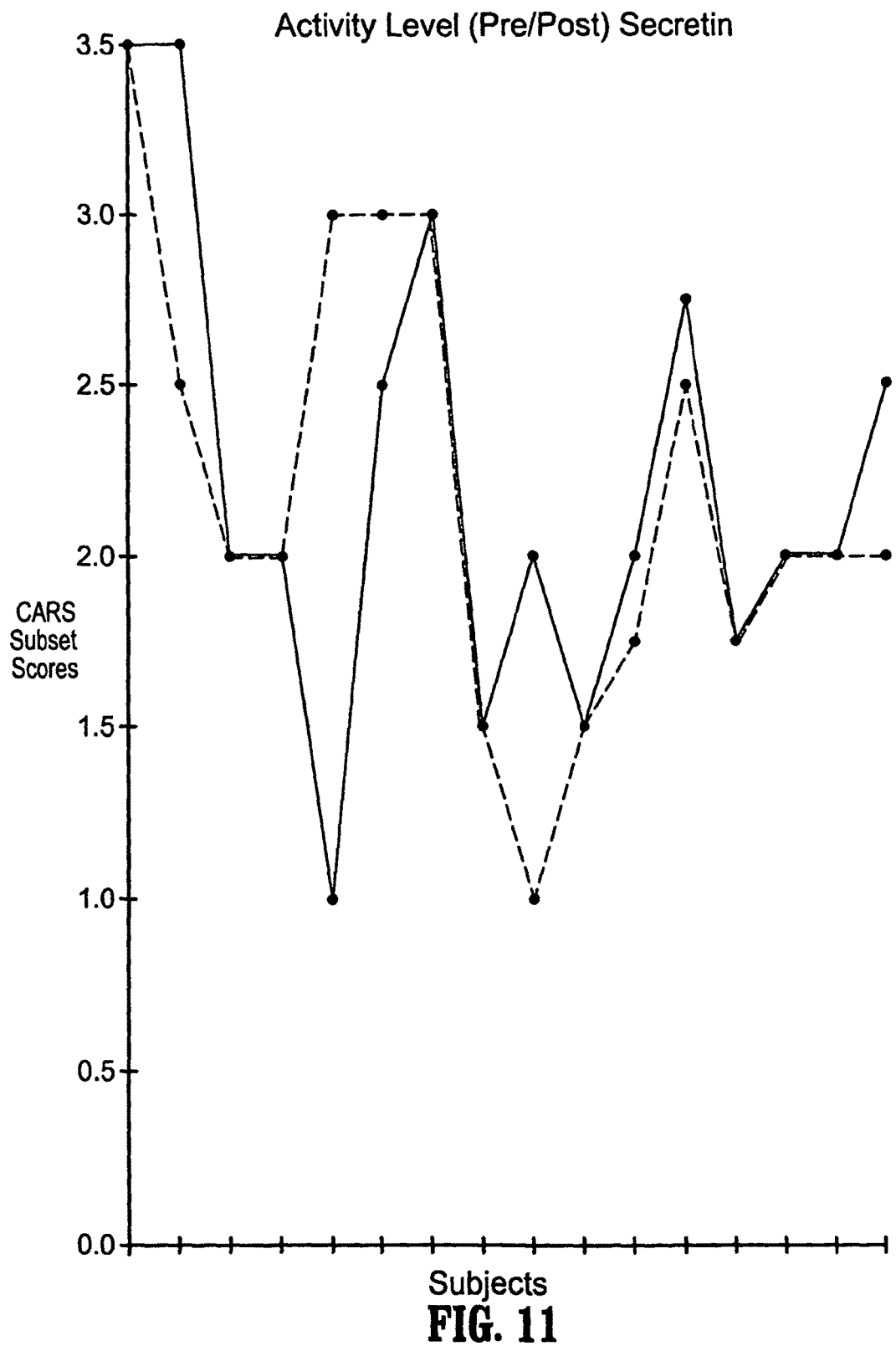
FIG. 11 illustrates the change in CARS scores for the sub-class Activity Level from pre-secretin administration to three weeks post-secretin administration, where the solid lines indicate pre-secretin scores and the dotted lines indicate post-secretin scores.
Figure 12:
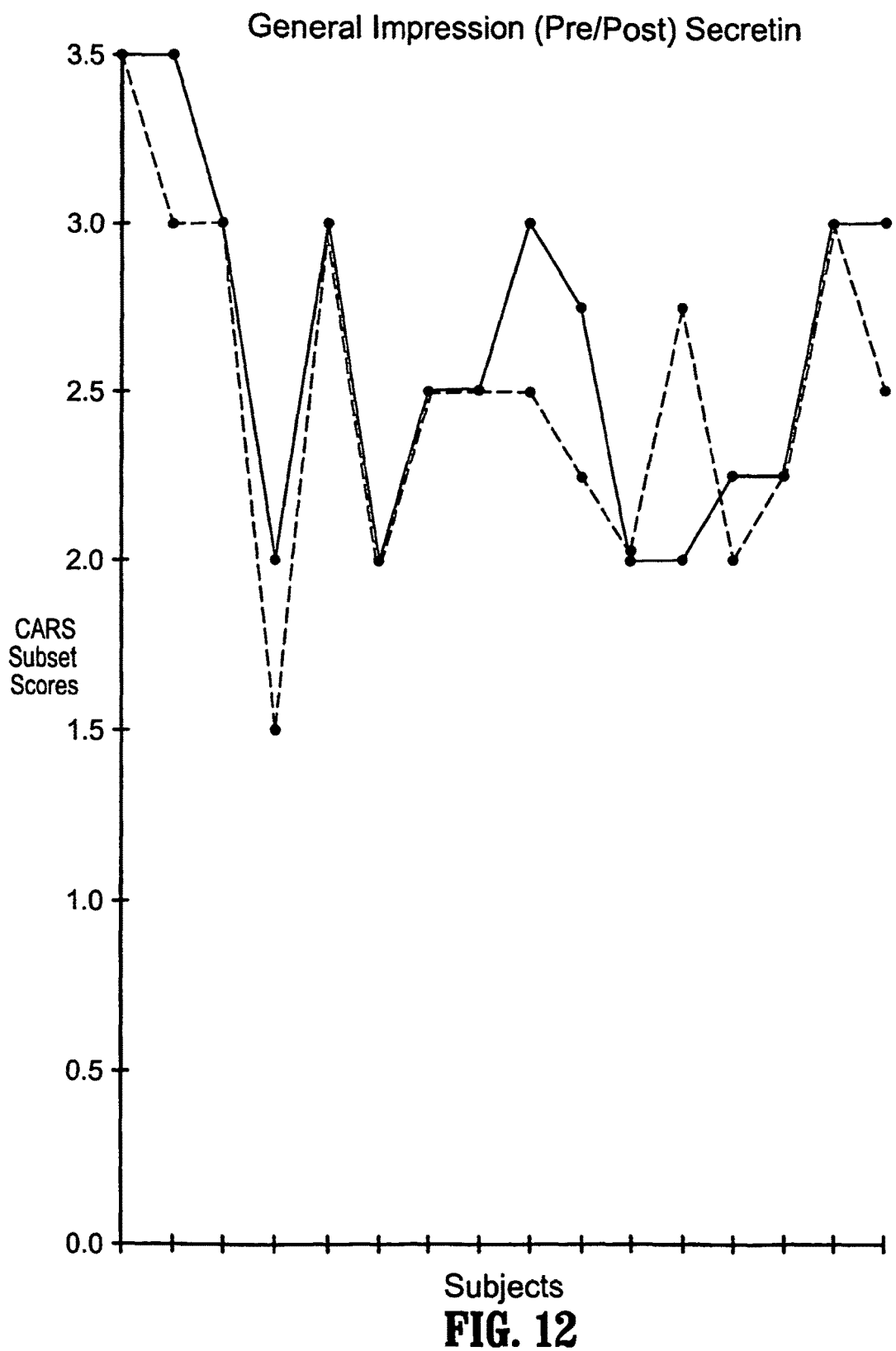
FIG. 12 illustrates the change in CARS scores for the sub-class General Impression from pre-secretin administration to three weeks post-secretin administration, where the solid lines indicate pre-secretin scores and the dotted lines indicate post-secretin scores.

In addition, FIG. 1 illustrates the pre-secretin CARS test results (solid line) and the post-secretin CARS test results (dotted line) for each of the 16 autistic children tested approximately 3 weeks after the first secretin administration. Most notably, FIG. 1 illustrates an overall decrease in the CARS scores indicating improvements in the PDD/autistic symptoms of the children. In particular, FIG. 2 illustrates respective percentage decreases in components of CARS scores, wherein the numbers represent percentage change in the average of the scores in each component of the CARS test post-secretin administration. In particular, FIGS. 3-12 illustrate the improved scores of each of the 16 autistic children for the individual components of the CARS scores. As shown, the component scores demonstrated improvement except for the fear component which increased 3 weeks post infusion.

II. Experiment 2

In this experiment, 37 autistic children with abnormal fecal chymotrypsin levels were administered secretin over the course of 6 months using the secretin infusion process described above. Their fecal chymotrypsin (FC) levels were measured weekly using the fecal chymotrypsin test described above.

Results of Experiment 2

Out of the 37 autistic children tested, the fecal chymotrypsin levels of 34 children had returned to normal after 6 months, the fecal chymotrypsin levels of 2 children moved to equivocal, and the fecal chymotrypsin level of 1 child remained abnormal. These results of this experiment are listed in the following Table 1.

TABLE 1

| Autistic Children Tested | Pre-Secretin Administration | 6 Months Post-Secretin Administration |
|---|---|---|
| # Autistic Children w/Abnormal FC levels | 37 | 1 |
| # Autistic Children w/Equivocal FC levels | 0 | 2 |
| # Autistic Children w/normal FC levels | 0 | 34 |

III. Experiment 3

Figure 15:
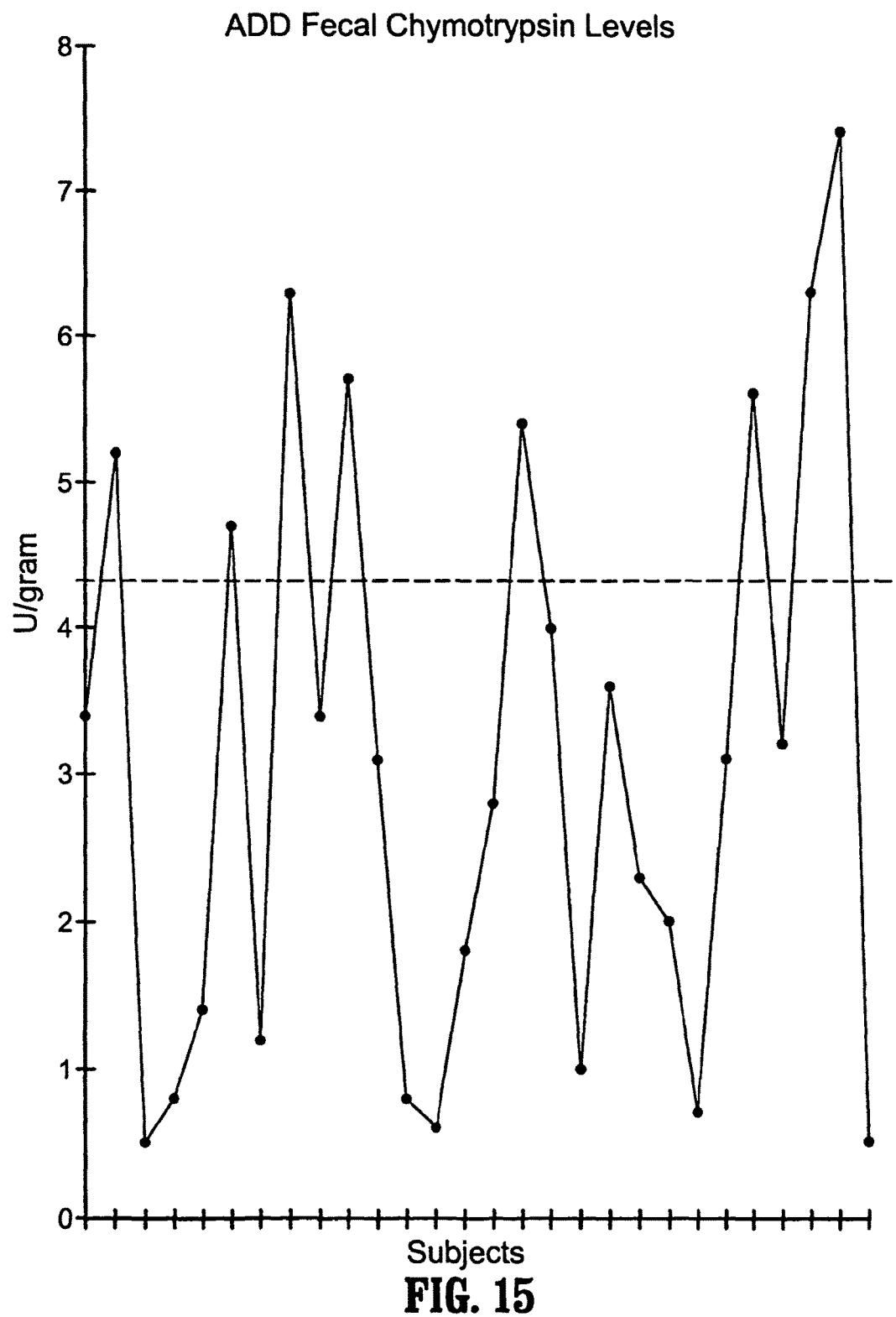
FIG. 15 illustrates the measured fecal chymotrypsin levels of 28 ADD children.

In this experiment, the fecal chymotrypsin levels of 28 children diagnosed with ADD were obtained using the fecal chymotrypsin test described above in Experiment 1. FIG. 15 illustrates the measured fecal chymotrypsin levels of these 28 children. It is to be noted that, as shown in FIG. 15, all of the 28 ADD children were found to have sub-normal fecal chymotrypsin levels since all of the values fell below 8.4 U/g. More specifically, 8 out of 28 children were determined to have an equivocal fecal chymotrypsin level and 20 out of the 28 children were determined to have a pathologic level of fecal chymotrypsin. As noted above, a chymotrypsin level of 8.4 U/g is considered a reference value for normal levels of chymotrypsin.

Of these 28 children who were diagnosed with ADD and abnormal fecal chymotrypsin levels, 10 were administered digestive enzymes comprising amylase, proteases, lipases, sucrase, maltase, and other digestive enzymes. These digestive enzymes were administered one tablet at each mealtime (i.e., three times a day), adjusted for the age and weight of the child. More specifically, for the ADD children ages 1-6, a quantity of digestive enzymes of approximately 4,000-8,000 U.S.P. Units/tablet comprising lipase, amylase and protease were administered. For the ADD children of ages 7-12, a quantity of digestive enzymes of approximately 8,000-12,000 U.S.P. Units/tablet comprising lipase, amylase and protease were administered. Other digestive enzymes that were administered in smaller quantities included cellulase, sucrase and maltase. These digestive enzymes were administered over a period of 6 months.

Results of Experiment 3

At the time of this experiment, 4 out of the 10 children who were administered the digestive enzymes were taking Ritalin. As is known in the art, Ritalin is a stimulant medication used to treat children and adults with ADD and ADHD. More specifically, it is used to treat hyperactivity and attention problems. As a result of the administration of the digestive enzymes, all of the 4 children who had been taking Ritalin were able to completely stop taking the Ritalin. In addition, significant improvements in the behavior of the other 6 children were noted. These results are shown in the following Table 2:

TABLE 2

| | |
|---|---|
| # ADD Children w/Sub-normal FC levels | 28 |
| # of the 28 ADD Children With Abnormal FC levels That Were Administered Digestive Enzymes | 10 |
| # of the 10 ADD Children That Were Administered Digestive Enzymes Who Were Taking Ritalin | 4 |
| # ADD Children Requiring Ritalin Administration 6 months Post Administration of Digestive Enzymes | 0 |

IV. Experiment 4

Figure 16:
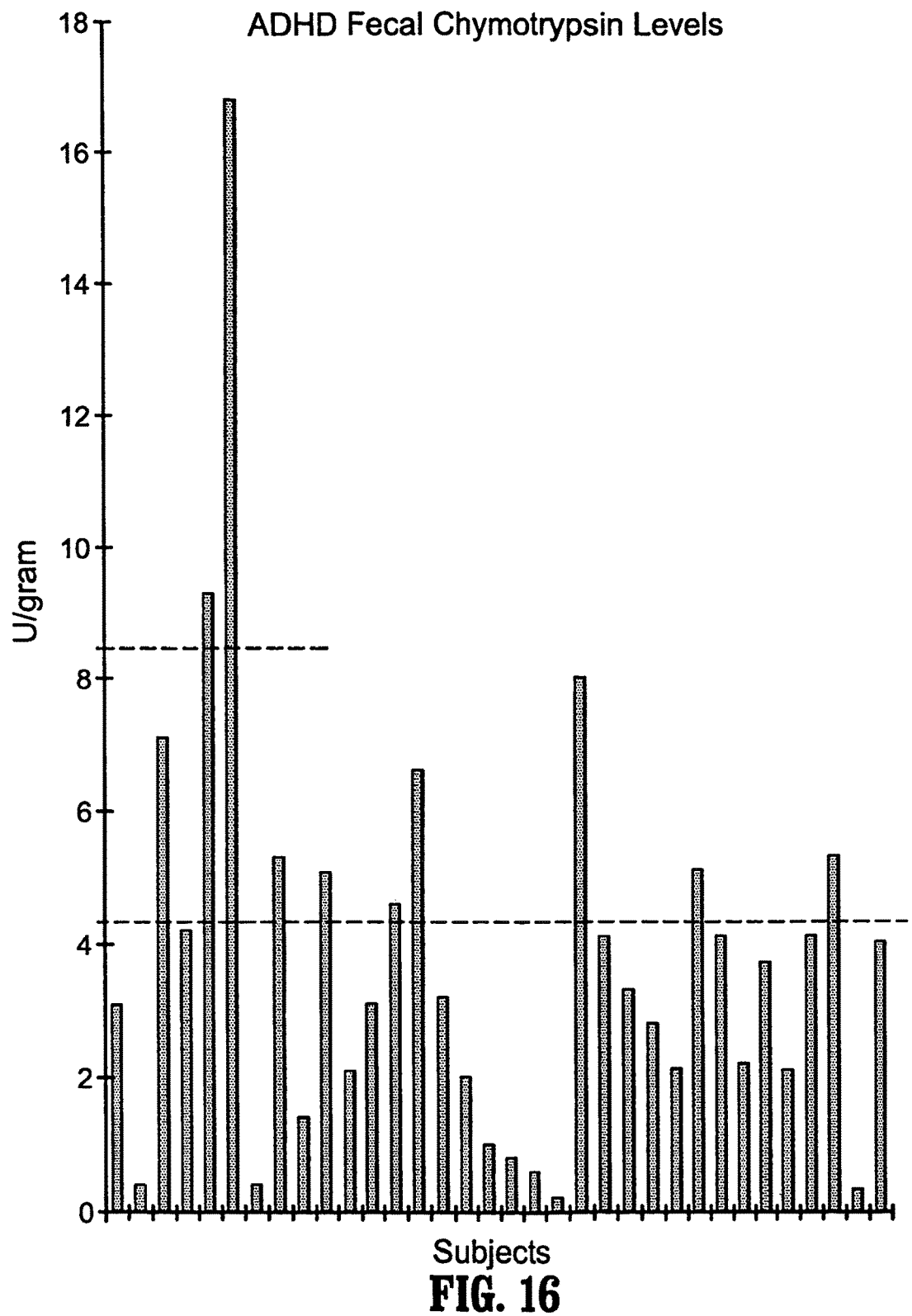
FIG. 16 illustrates the measured fecal chymotrypsin levels of 34 ADHD children.

In this experiment, the fecal chymotrypsin levels of 34 children diagnosed with ADHD were obtained using the fecal chymotrypsin test described above in Experiment 1, the levels of which are illustrated in FIG. 16. As shown, 32 children out of 34 children tested were determined to have sub-normal fecal chymotrypsin levels. It is to be further noted that 24 of the 34 children were found to have pathologic levels of fecal chymotrypsin.

To determine the effect of secretin administration on ADHD children, 5 of the 24 children having a pathologic fecal chymotrypsin level were administered secretin using the secretin infusion process described above.

Results of Experiment 4

Figure 17:
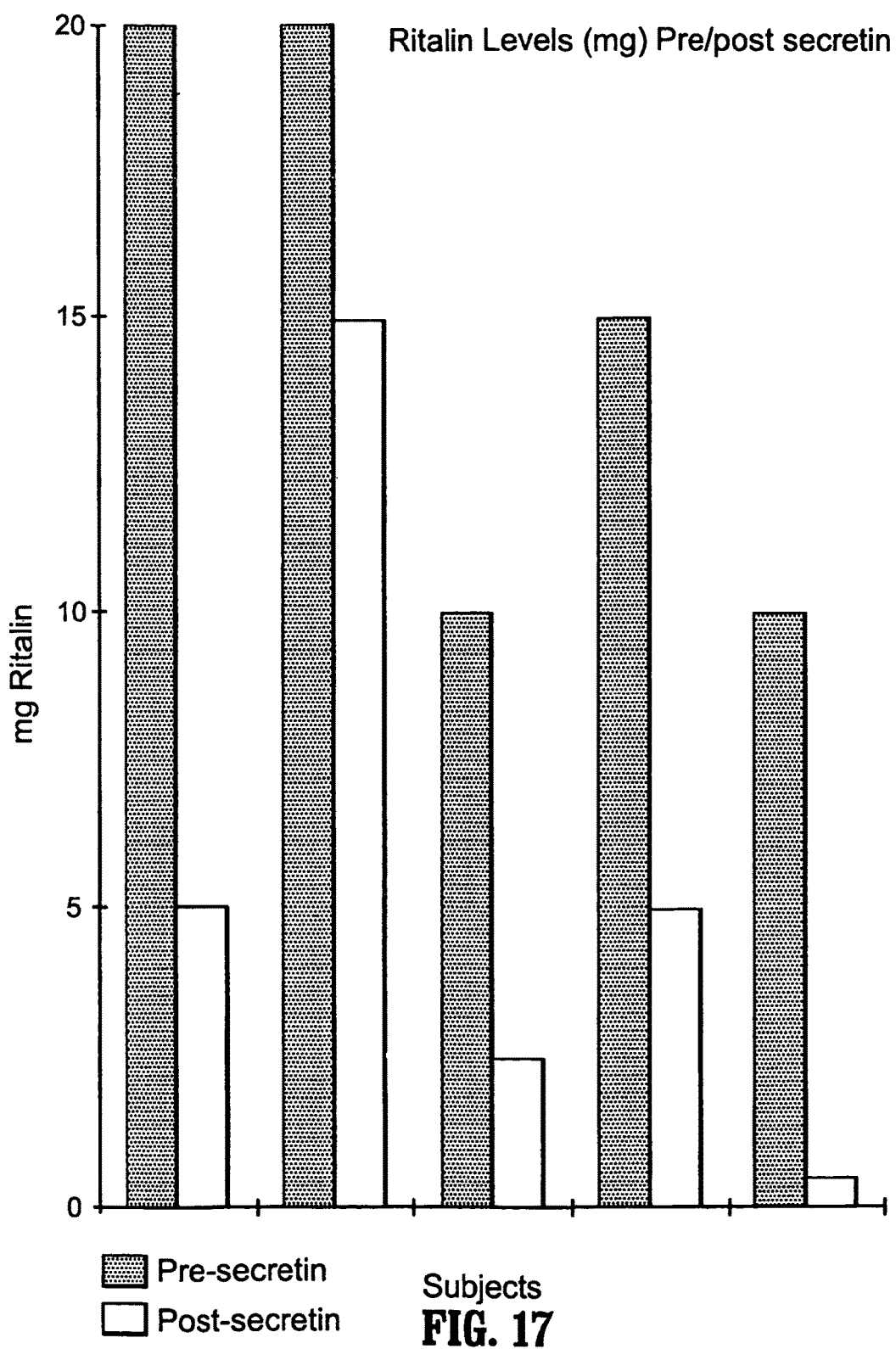
FIG. 17 illustrates Ritalin levels administered before and after secretin administration in five of the ADHD children in FIG. 16, where the shaded bars indication pre-secretin Ritalin levels and the non-shaded bars indicate post-secretin Ritalin levels.

The results of this experiment are set forth in FIG. 17, which illustrates the required levels of Ritalin (in mg) of the 5 children tested both pre-secretin administration (as indicated by the shaded bars) and 6 months post-secretin administration (as indicated by the non-shaded bars). It is to be appreciated that as shown in FIG. 17, each of the 5 children who were administered secretin demonstrated significant changes post-secretin administration with respect to the level of Ritalin (mg) that each child needed to remain at the same functional level as their functional level prior to secretin administration.

V. Experiment 5

In this experiment, to determine the effect of the administration of digestive enzymes to ADHD children, 9 children of the 34 children diagnosed with ADHD (in experiment 4 described above) whose fecal chymotrypsin levels were determined to be pathologic were administered digestive enzymes. Such digestive enzymes included amylase, lipase, proteases, sucrases, maltase, and other digestive enzymes. Each child was administered 1 tablet of digestive enzymes at each mealtime (i.e., three times a day), adjusted for age and weight of the child. More specifically, for the ADHD children ages 1-6, a quantity of digestive enzymes of approximately 4,000-8,000 U.S.P. Units/tablet comprising lipase, amylase and protease were administered. For the ADHD children of ages 7-12, a quantity of digestive enzymes of approximately 8,000-12,000 U.S.P. Units/tablet comprising lipase, amylase and protease were administered. Other digestive enzymes that were administered in smaller quantities included cellulase, sucrase and maltase. The digestive enzymes were administered over a 6 month period.

Results of Experiment 5

It is to be appreciated that as a result of the administration of digestive enzymes over the 6 month period, all 9 children were able to reduce their required Ritalin levels. Most notably, 2 of the 9 children were able to stop taking Ritalin after 6 months of digestive enzyme administration. The results of experiment 5 are illustrated in the following Table 3:

TABLE 3

| | |
|---|---|
| # ADHD Children w/Abnormal FC levels Who Were Administered Digestive Enzymes | 9 |
| # Of The 9 ADHD Children Whose Ritalin Levels Were Reduced 6 months Post-Digestive Enzyme Administration | 9 |
| # Of The 9 ADHD Children Who Stopped Taking Ritalin 6 Months Post-Digestive Enzyme Administration | 2 |

VI. Experiment 6

The following experiment was performed to determine the effect of the administration of digestive enzymes to Autistic children. In this experiment, the fecal chymotrypsin levels of 17 autistic children of varying ages were measured (pre-digestive enzyme administration) using the method described above in Experiment 1. In addition, the fecal chymotrypsin levels of these 17 children were measured 6 months post digestive enzyme administration after receiving digestive enzyme therapy as described below. The following table demonstrates the measured fecal chymotrypsin levels of these 17 children:

TABLE 4

| Patient | Age | Pre-DE Administration Fecal Chymotrypsin Levels | 6-Months Post-DE Administration Fecal Chymotrypsin Levels |
|---|---|---|---|
| 1 | 2.5 | 3.3 | 7.1 |
| 2 | 7 | 1.5 | 3.8 |
| 3 | 9 | 4.0 | 7.8 |
| 4 | 3.5 | 2.0 | 10.2 |
| 5 | 5 | 3.3 | 8.0 |
| 6 | 4 | 1.0 | 6.8 |
| 7 | 8 | 1.6 | 10.2 |
| 8 | 6 | 4.0 | 12.2 |
| 9 | 7 | 6.8 | 14.9 |
| 10 | 3 | 2.8 | 6.2 |
| 11 | 5 | 3.4 | not available |
| 12 | 3 | 2.0 | 4.0 |
| 13 | 2 | 4.0 | 4.6 |
| 14 | 11 | 3.3 | 5.0 |
| 15 | 9 | 2.2 | 9.2 |
| 16 | 8 | 1.4 | 12.0 |
| 17 | 7 | 3.8 | 6.0 |

As illustrated, each of the 17 autistic children were found to have either sub-normal or pathologic fecal chymotrypsin levels. In particular, the fecal chymotrypsin level of patient #9 was found to be sub-normal as it fell below 8.4 U/g and the fecal chymotrypsin levels of the remaining 16 children were found to be pathologic since the levels fell below 4.2 U/g. Each of the 17 autistic children were administered digestive/pancreatic enzymes comprising amylases, proteases, lipases, sucrases, maltases, and other digestive/pancreatic enzymes including trypsin and chymotrypsin. The digestive enzymes were administered on a daily basis at each mealtime, preferably 3-6 times per day. The quantity of digestive enzymes was adjusted for the weight and ages of the child. For instance, depending on the weight and age of the child, a preferred quantity of lipases ranges from 4,000-20,000 U.S.P., a preferred quantity of proteases ranges from 10,000-50,000 U.S.P., a preferred quantity of amylases ranges from 10,000-60,000 U.S.P., a preferred quantity of pancreatin (pancreatic extract) ranges from 2,000-6,000 U.S.P., a preferred quantity of chymotrypsin ranges from 2-5 mg and a preferred quantity of trypsin ranges from 60-100 mg. In addition, any combination of two or more types of any of the above digestive enzymes may be administered.

Results of Experiment 6

As illustrated in Table 4, the measured fecal chymotrypsin levels of at least 16 of the 17 autistic children were found to increase 6 months post-digestive enzyme administration. Most notably, the fecal chymotrypsin levels of 5 children (patients #4, 7, 8, 15, and 16) that were initially found to be pathologic had increased to the normal range 6 months post-digestive enzyme administration.

Furthermore, a notable decrease in autistic symptomotology of each of the 17 autistic children was observed as a result of digestive/pancreatic enzyme administration. These observations are outlined in the following tables. Table 5 outlines the responses that were reported after administration of digestive enzymes to the autistic children in the range of ages 2-4 (i.e., 6 of the 17 children listed in Table 4). Each numeric entry in Table 5 indicates the number of children (of the 6 children ages 2-4) exhibiting the corresponding behavior.

TABLE 5

| Behavior | Pre-DE | 3 Months Post-DE | 6 Months Post-DE |
|---|---|---|---|
| some eye contact | 0 | 2 | 5 |
| toilet trained | 1 | 2 | 3 |
| some toilet training (not included above) | 2 | 3 | not available |
| some speech | 2 | 3 | 6 |
| formed bowel movement | 1 | 2 | 6 |
| hyperactive | 5 | 3 | 1 |
| plays with others | 0 | 2 | 4 |
| hand flapping | 4 | 2 | 1 |

Furthermore, Table 6 outlines the responses that were reported after administration of digestive enzymes the autistic children of ages 5-12 (i.e., 11 of the 17 children listed in Table 4). Again, each numeric entry in Table 6 indicates the number of children (of the 11 children ages 5-12) exhibiting the corresponding behavior.

TABLE 6

| Behavior | Pre-DE | 3 Months Post-DE | 6 Months Post-DE |
| --- | --- | --- | --- |
| some eye contact | 8 | 6 | 8 |
| toilet trained | 3 | 6 | 6 |
| some toilet training (not included above) | 2 | not available | 4 |
| some speech | 6 | 8 | 10 |
| formed bowel movement | 2 | 7 | 10 |
| hyperactive | 9 | 5 | 3 |
| plays with others | 3 | 5 | 8 |
| hand flapping | 6 | 5 | 1 |

In summary, the results of the experiments described herein demonstrate that the fecal chymotrypsin level of an individual having one or more developmental disorders falling within the spectrum of PDD can be used as a marker to determine the benefit of administering secretin, other neuropeptides, peptides and/or digestive enzymes to the individual. Indeed, the above experiments indicate that the administration of secretin, other neuropeptides, peptides and/or digestive enzymes to children suffering from a disorder such as autism, ADD and ADHD, for example, and having sub-normal to pathologic levels of fecal chymotrypsin, will result in the amelioration of symptomatologies of such disorders.

Although illustrative embodiments have been described herein with reference to the accompanying drawings, it is to be understood that the present invention is not limited to those precise embodiments, and that various other changes and modifications may be affected therein by one skilled in the art without departing from the scope or spirit of the invention. All such changes and modifications are intended to be included within the scope of the invention as defined by the appended claims.

The invention claimed is:

1. A method for determining if an individual having a Pervasive Developmental Disorder (PDD) and a subnormal level of fecal chymotrypsin has improved after administration of a dose of digestive enzymes; the method comprising:
  a) making a quantitative pre-administration measurement of a symptom of a PDD and measuring a pre-administration level of fecal chymotrypsin in the individual;
  b) administering to the individual a dose of digestive enzymes if the individual has a subnormal level of fecal chymotrypsin, wherein the digestive enzymes comprise a protease, an amylase and a lipase;
  c) making a quantitative post-administration measurement of the symptom of the PDD and measuring a post-administration level of fecal chymotrypsin in the individual; and
  d) comparing the quantitative post-administration measurement of the symptom of the PDD to a quantitative pre-administration measurement of the symptom of the PDD,
  wherein a decrease in the quantitative post-administration measurement of the symptom compared to the quantitative pre-administration of the symptom indicates the PDD has improved.

2. The method of claim 1, wherein the quantitative, post-administration measurement measures social behavior.

3. The method of claim 1, wherein the quantitative, post-administration measurement measures imitation.

4. The method of claim 1, wherein the quantitative, post-administration measurement measures body use.

5. The method of claim 1 wherein the quantitative, post-administration measurement measures object use.

6. The method of claim 1, wherein the quantitative, post-administration measurement measures adaptation to change.

7. The method of claim 1 wherein the quantitative, post-administration measurement measures visual response.

8. The method of claim 1, wherein the quantitative, post-administration measurement measures listening response.

9. The method of claim 1, wherein the quantitative, post-administration measurement measures taste, smell, touch response and use.

10. The method of claim 1, wherein the quantitative, post-administration measurement measures fear.

11. The method of claim 1, wherein the quantitative, post-administration measurement measures verbal communication.

12. The method of claim 1, wherein the quantitative, post-administration measurement measures non-verbal communication.

13. The method of claim 1, wherein the quantitative, post-administration measurement measures activity level.

14. The method of claim 1, wherein the measurement is a quantitative measurement of general impression.

15. The method of claim 1, wherein the quantitative, post-administration measurement is a Childhood Autism Rating Scale measurement.

16. The method of claim 1, wherein the digestive enzymes comprise a protease that comprises chymotrypsin or trypsin.

17. The method of claim 1, wherein measuring a pre-administration level of fecal chymotrypsin comprises enzyme spectrophotometry.

18. The method of claim 1, wherein measuring a post-administration level of fecal chymotrypsin comprises enzyme spectrophotometry.

19. A method for determining if an individual having a Pervasive Developmental Disorder (PDD) and a subnormal level of fecal chymotrypsin has improved after administration of a dose of digestive enzymes; the method comprising:
  a) making a quantitative pre-administration measurement of a symptom of a PDD and measuring a pre-administration level of fecal chymotrypsin in the individual;
  b) administering to the individual a dose of digestive enzymes if the individual has a subnormal level of fecal chymotrypsin, wherein the digestive enzymes comprise a protease, an amylase and a lipase;
  c) making a quantitative post-administration measurement of the symptom of the PDD and measuring a post-administration level of fecal chymotrypsin in the individual; and
  d) comparing the quantitative post-administration measurement of the symptom of the PDD to a quantitative pre-administration measurement of the symptom of the PDD,
  wherein an improvement in the quantitative post-administration measurement of the symptom compared to the quantitative pre-administration of the symptom indicates that the PDD has improved.

20. The method of claim 19, wherein the quantitative, post-administration measurement measures social behavior.

21. The method of claim 19, wherein the quantitative, post-administration measurement measures imitation.

22. The method of claim 19, wherein the quantitative, post-administration measurement measures visual response.

23. The method of claim 19, wherein the quantitative, post-administration measurement measures listening response.

24. The method of claim 19, wherein the quantitative, post-administration measurement measures taste, smell, touch response and use.

25. The method of claim 19, wherein the quantitative, post-administration measurement is a Childhood Autism Rating Scale measurement.

26. The method of claim 19, wherein the digestive enzymes comprise a protease that comprises chymotrypsin or trypsin.

27. The method of claim 19, wherein measuring a pre-administration level of fecal chymotrypsin comprises enzyme spectrophotometry.

28. The method of claim 19, wherein measuring a post-administration level of fecal chymotrypsin comprises enzyme spectrophotometry.

* * * * *